(12) United States Patent
Liu et al.

(10) Patent No.: US 7,786,045 B2
(45) Date of Patent: Aug. 31, 2010

(54) ARYL ETHER COMPOUNDS AND THEIR PREPARATION AND USE THEREOF

(75) Inventors: Changling Liu, Shenyang (CN); Miao Li, Shenyang (CN); Liwen Geng, Shenyang (CN); Hong Zhang, Shenyang (CN); Defeng Zhou, Shenyang (CN); Dongliang Cui, Shenyang (CN); Yanmei Luo, Shenyang (CN); Zhinian Li, Shenyang (CN)

(73) Assignees: Sinochem Corporation, Beijing (CN); Shenyang Research Institute of Chemical Industry, Shenyang (CN)

( * ) Notice: Subject to any disclaimer, the term of this patent is extended or adjusted under 35 U.S.C. 154(b) by 430 days.

(21) Appl. No.: 11/817,996

(22) PCT Filed: May 15, 2006

(86) PCT No.: PCT/CN2006/000971

§ 371 (c)(1),
(2), (4) Date: Sep. 7, 2007

(87) PCT Pub. No.: WO2006/125370

PCT Pub. Date: Nov. 30, 2006

(65) Prior Publication Data

US 2008/0275070 A1   Nov. 6, 2008

(30) Foreign Application Priority Data

May 26, 2005   (CN) .................. 2005 1 0046515

(51) Int. Cl.
*C07D 231/10* (2006.01)
*C07D 261/06* (2006.01)
*C07D 413/04* (2006.01)
*A01N 43/56* (2006.01)
*A01N 43/80* (2006.01)

(52) U.S. Cl. .................. 504/282; 548/364.1
(58) Field of Classification Search ............. 548/364.1; 504/282

See application file for complete search history.

(56) References Cited

U.S. PATENT DOCUMENTS

| 5,021,581 A | 6/1991 | Clough |
| 6,031,110 A | 2/2000 | Kirstgen et al. |
| 2008/0108668 A1 | 5/2008 | Liu |

FOREIGN PATENT DOCUMENTS

| CN | 1030749 | 2/1989 |
| CN | 1100761 | 3/1998 |
| CN | 1046275 | 11/1999 |
| CN | 1657524 | 8/2005 |
| EP | 0811614 | 12/1997 |

OTHER PUBLICATIONS

English translation of Written Opinion ISA 237 mailed in PCT/CN2006/000971 on Aug. 31, 2006.

*Primary Examiner*—Kahsay T Habte
(74) *Attorney, Agent, or Firm*—Smith, Gambrell & Russell, LLP

(57) ABSTRACT

The invention relates to aryl ether compounds and its preparation method and use thereof. The aryl ether compounds of the invention having general formula (I):

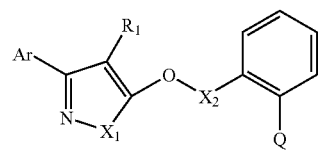

The groups are as defined as specification. The aryl ether compounds of present invention have wide spectrum fungicidal activity, and may be used to control diseases in all sorts of plants caused by oomycete, basidiomycete, ascomycete pathogens and deuteromycete. The some of the compounds have very good insecticidal and acaricidal activity, and may be used to control insects and mites.

9 Claims, No Drawings

ARYL ETHER COMPOUNDS AND THEIR PREPARATION AND USE THEREOF

FIELD OF THE INVENTION

The invention relates to fungicide or insecticide, specifically to an aryl ether compounds and their preparation and use thereof.

BACKGROUND OF THE INVENTION

Methoxyacrylate compounds are natural products and known with biological active. Fungicide pyraclostrobin with broad spectrum was disclosed in U.S. Pat. No. 5,869,517, U.S. Pat. No. 6,054,592, CN1154692 and CN1308065. The structure of pyraclostrobin is as follows:

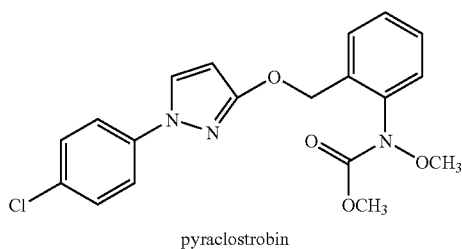

pyraclostrobin

The following Compound with fungicidal activity was also disclosed in DE19548786:

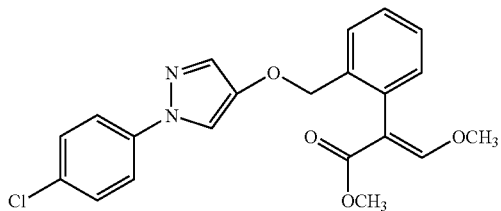

The following Compound with fungicidal activity is known in patent WO9933812:

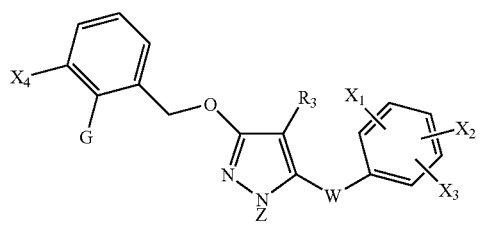

The following Compound with fungicidal activity is known in *Nongyaoxue Xuebao*, 2004, 6(1), 17-21:

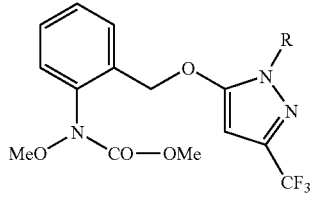

Before this invention, we applied CN1657524A and WO2005080344A, which relates to fungicide or insecticide, especifically to substituted azole compounds having general formula, below:

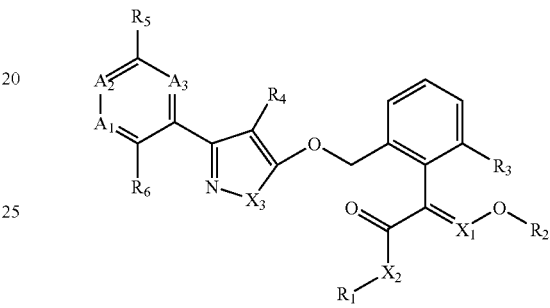

wherein: $X_1$ is selected from CH or N; $X_2$ is selected from O, S or $NR_7$; $R_7$ is selected from H or $C_1$-$C_{12}$alkyl; $X_3$ is selected from O, S or $NR_8$; $R_8$ is selected from H, $C_1$-$C_{12}$alkyl; $C_1$-$C_{12}$haloalkyl; $C_1$-$C_{12}$alkoxycarbonyl or $C_1$-$C_{12}$alkoxycarbonyl$C_1$-$C_{12}$alkyl; $R_1$, $R_2$ is independently selected from H, $C_1$-$C_{12}$alkyl or $C_1$-$C_{12}$haloalkyl; $A_1$ is selected from N or $CR_9$; $A_2$ is selected from N or $CR_{10}$; $A_3$ is selected from N or $CR_{11}$; if $A_1$ is selected from N, $A_2$ is selected from $CR_{10}$, $A_3$ is selected from $CR_{11}$; if $A_2$ is selected from N, $A_1$ is selected from $CR_9$, $A_3$ is selected from $CR_{11}$; if $A_3$ is selected from N, $A_1$ is selected from $CR_9$, $A_2$ is selected from $CR_{10}$; $R_3$ is selected from H, halo, $C_1$-$C_{12}$alkyl, $C_1$-$C_{12}$haloalkyl or $C_1$-$C_{12}$alkoxy; $R_4$, $R_5$, $R_6$, $R_9$, $R_{10}$ and $R_{11}$ may be the same or different, selected from H, halo, $NO_2$, CN, $CONH_2$, $CH_2CONH_2$, $CH_2CN$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$alkylsulfonyl, $C_1$-$C_{12}$alkylcarbonyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, or the group may be substituted by any other group consisting of amino$C_1$-$C_{12}$alkyl, aroxyl, aryl$C_1$-$C_{12}$alkoxy, aryl, heteroaryl, aryl$C_1$-$C_{12}$alkyl, heteroaryl$C_1$-$C_{12}$alkyl, heteroaryl$C_1$-$C_{12}$alkoxy.

The compounds disclosed above patents (applications) were similar to this invention, but there are some obvious differences.

SUMMARY OF THE INVENTION

The aim of the present invention is to provide the aryl ether compounds with biological activity against all sorts of plant disease and insects at very low dosage and the compounds can be applied in agriculture to control disease and insects in plant.

Detailed description of the invention is as follows:

The present invention offered an aryl ether compounds having general formula I:

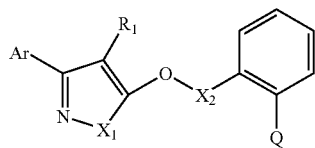

Wherein: $X_1$ is selected from O, S or $NR_2$;

$X_2$ is selected from $CH_2$ or

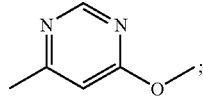

If $X_2$ is selected from

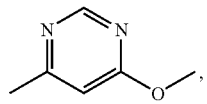

pyrimidine-4 is combined with O, pyrimidine-6 is combined with phenyl.

$R_1$ is selected from H, halo, $NO_2$, CN, $CONH_2$, $CH_2CONH_2$, $CH_2CN$; $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$alkylsulfonyl, $C_1$-$C_{12}$alkylcarbonyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, substituted or unsubstituted amino$C_1$-$C_{12}$alkyl;

$R_2$ is selected from H, $C_1$-$C_{12}$alkyl, $C_1$-$C_{12}$haloalkyl, $C_1$-$C_{12}$alkoxycarbonyl or $C_1$-$C_{12}$alkoxycarbonyl$C_1$-$C_{12}$alkyl;

Q is selected from one of the following group:

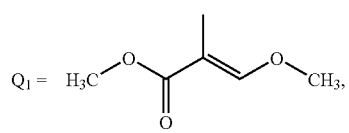

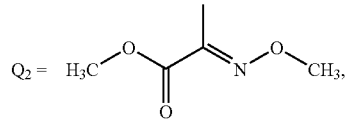

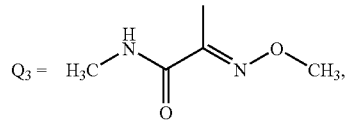

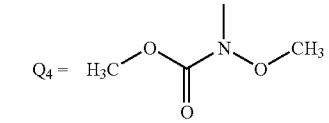

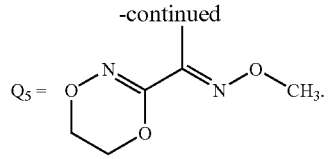

If Q is selected from $Q_1$, $Q_2$, $Q_3$ or $Q_5$, $X_2$=$CH_2$, Ar is selected from substituted or unsubstituted five member heteroaryl; if

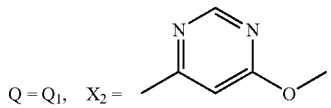

or if Q=$Q_4$, $X_2$=$CH_2$, Ar is selected from substituted or unsubstituted aryl, heteroaryl; the substitution group may be selected from halo, CN, $NO_2$, $C_1$-$C_6$alkyl, $C_1$-$C_6$alkoxy, $C_1$-$C_6$alkylthio, $C_1$-$C_6$alkylsulfonyl, $C_1$-$C_6$alkoxycarbonyl, $C_1$-$C_6$haloalkoxy, substituted aryl or substituted aroxyl and stereoisomer.

The preferred compounds of general formula I of this invention are:

$X_1$ is selected from O, S or $NR_2$;

$X_2$ is selected from $CH_2$ or

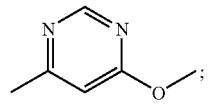

$R_1$ is selected from H, halo, $NO_2$, CN, $CONH_2$, $CH_2CONH_2$, $CH_2CN$; $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl, $C_1$-$C_6$alkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, substituted or unsubstituted amino$C_1$-$C_6$alkyl;

$R_2$ is selected from H, $C_1$-$C_6$alkyl, $C_1$-$C_6$haloalkyl, $C_1$-$C_6$alkoxycarbonyl or $C_1$-$C_6$alkoxycarbonyl$C_1$-$C_6$alkyl;

If Q is selected from $Q_1$, $Q_2$, $Q_3$ or $Q_5$, $X_2$=$CH_2$, Ar is selected from substituted or unsubstituted five member heteroaryl; if

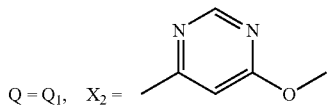

or if Q=$Q_4$, $X_2$=$CH_2$, Ar is selected from substituted or unsubstituted aryl, heteroaryl; the substitution group may be selected from halo, CN, $NO_2$, $C_1$-$C_6$alkyl, $C_1$-$C_6$alkoxy, $C_1$-$C_6$alkylthio, $C_1$-$C_6$alkylsulfonyl, $C_1$-$C_6$alkoxycarbonyl, $C_1$-$C_6$haloalkoxy, substituted phenyl or substituted phenoxy.

Furthermore, the preferred compounds of general formula I of this invention are:

$X_1$ is selected from O or $NR_2$;

$X_2$ is selected from $CH_2$ or

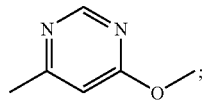

$R_1$ is selected from H, halo, $NO_2$, CN, $CONH_2$, $CH_2CONH_2$, $CH_2CN$; $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl, $C_1$-$C_6$alkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, substituted or unsubstituted amino$C_1$-$C_3$alkyl;

$R_2$ is selected from H, $C_1$-$C_6$alkyl, $C_1$-$C_6$haloalkyl, $C_1$-$C_3$alkoxycarbonyl or $C_1$-$C_6$alkoxycarbonyl$C_1$-$C_3$alkyl;

If Q is selected from $Q_1$, $Q_2$, $Q_3$ or $Q_5$, $X_2$=$CH_2$, Ar is selected from substituted or unsubstituted furan, thiophen or thiazol; if

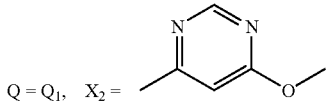

or if Q=$Q_4$, $X_2$=$CH_2$, Ar is selected from substituted or unsubstituted phenyl, pyridine, furan, thiophen or thiazol; the substitution group may be selected from halo, CN, $NO_2$, $C_1$-$C_6$alkyl, $C_1$-$C_6$alkoxy, $C_1$-$C_6$alkylthio, $C_1$-$C_6$alkylsulfonyl, $C_1$-$C_6$haloalkoxy, substituted phenyl or substituted phenoxy.

Even more preferred compounds of formula I of this invention are:

$X_1$ is selected from O or $NR_2$;

$X_2$ is selected from $CH_2$ or

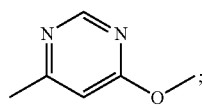

$R_1$ is selected from H, Cl, Br, F, $NO_2$, $CH_2CN$ or $C_1$-$C_6$alkyl;

$R_2$ is selected from H, $C_1$-$C_3$alkyl, $C_1$-$C_3$haloalkyl, $C_1$-$C_3$alkoxycarbonyl or $C_1$-$C_3$alkoxycarbonyl$C_1$-$C_3$alkyl;

If Q is selected from $Q_1$, $Q_2$, $Q_3$ or $Q_5$, $X_2$=$CH_2$, Ar is selected from substituted or unsubstituted furan, thiophen or thiazol; if

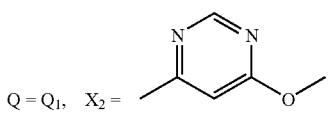

or if Q=$Q_4$, $X_2$=$CH_2$, Ar is selected from substituted or unsubstituted phenyl, pyridine, furan or thiophen or thiazol; the substitution groups may be selected from halo, CN, $NO_2$, $C_1$-$C_6$alkyl, $C_1$-$C_6$alkoxy, $C_1$-$C_6$alkylthio, $C_1$-$C_6$haloalkoxy, chloro phenyl or chloro phenoxy.

Most preferred compounds of formula I of this invention are:

$X_1$ is selected from O or $NR_2$;

$X_2$ is selected from $CH_2$ or

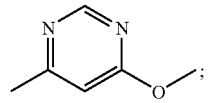

$R_1$ is selected from H or methyl;

$R_2$ is selected from H, methyl or isopropyl;

If Q is selected from $Q_1$, $Q_2$, $Q_3$ or $Q_5$, $X_2$=$CH_2$, Ar is selected from substituted or unsubstituted furan or thiophen; if

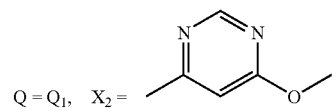

or if Q=$Q_4$, $X_2$=$CH_2$, Ar is selected from substituted or unsubstituted phenyl, pyridine, furan or thiophen; the substitution groups may be selected from halo, $C_1$-$C_3$alkyl, $C_1$-$C_3$alkoxy, $C_1$-$C_3$alkylthio or $C_1$-$C_3$haloalkoxy.

The following is the meaning of terms in the general formula I:

The unsubstituted ones refer to all the substitute group is H.

Amino may be substituted by 1-2 groups, selected from $C_1$-$C_3$alkyl, $C_1$-$C_3$alkoxy, halo$C_1$-$C_3$alkyl, halo$C_1$-$C_3$alkoxy, halo, $NO_2$ or CN etc.

Phenyl, benzyl, phenoxy, benzyloxy may be substituted by 1-5 groups, selected from alkyl, alkoxy, haloalkyl, haloalkoxy, halo, $NO_2$ or CN etc.

Halogen or halo is fluorine, chlorine, bromine or iodine.

The alkyl is to be understood as meaning straight-chain or branched alkyl, such as methyl, ethyl, propyl, isopropyl or tert-butyl.

The haloalkyl refers to straight or branched chain alkyl, in which hydrogen atom may be all or partly substituted with halogen, such as chloromethyl, dichloromethyl, trichloromethyl, fluoromethyl, difluoromethyl, trifluoromethyl.

The alkoxy refers to straight or branched chain alkyl, which is linked to the structure by oxygen atom.

The haloalkoxy refers to straight or branched chain alkoxy, in which hydrogen atom may be all or partly substituted with halogen, such as chloromethoxy, dichloromethoxy, trichloromethoxy, fluoromethoxy, difluoromethoxy, trifluoromethoxy, chlorofluoromethoxy or trifluoroethoxy.

The alkenyl refers to a straight or branched, having double bonds at any position such as vinyl or allyl. Substituted alkenyl includes arylvinyl which is substituted at any position with any group.

The alkynyl refers to a straight or branched, having triple bonds at any position. Such as ethynyl, propynyl. Substituted alkynyl includes arylethynyl which is substituted at any position with any group.

The aryl and aryl in arylalkyl, arylalkenyl, arylalkynyl, aryloxy and aryloxyalkyl include phenyl or naphthyl.

The hetero aryl in this invention refers to five member ring or six member ring containing one or more N, O, S hetero atoms. Such as pyridine, furan, pyrimidine, pyrazine, pyridazine, triazine, quinoline or benzofuran.

Because of the C=C or C=N link to different substituted group, the compounds of the invention may form geometrical isomer (the different isomers are respectively expressed with Z and E). Z isomer and E isomer and their mixtures in any proportion are included in the invention.

The present invention is explained by the following compounds in table 1, but without being restricted thereby.

TABLE 1

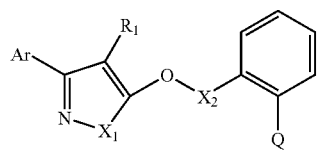

I

| number | $X_1$ | $X_2$ | $R_1$ | Ar | Q |
|---|---|---|---|---|---|
| 1 | $NCH_3$ | $CH_2$ | H | $C_6H_5$ | $Q_4$ |
| 2 | $NCH_3$ | $CH_2$ | H | 4-Cl—$C_6H_4$ | $Q_4$ |
| 3 | $NCH_3$ | $CH_2$ | H | 4-F—$C_6H_4$ | $Q_4$ |
| 4 | $NCH_3$ | $CH_2$ | H | 4-$NO_2$—$C_6H_4$ | $Q_4$ |
| 5 | $NCH_3$ | $CH_2$ | H | 4-$CF_3$—$C_6H_4$ | $Q_4$ |
| 6 | $NCH_3$ | $CH_2$ | H | 4-CN—$C_6H_4$ | $Q_4$ |
| 7 | $NCH_3$ | $CH_2$ | H | 4-$CH_3CO_2$—$C_6H_4$ | $Q_4$ |
| 8 | $NCH_3$ | $CH_2$ | H | 4-$CH_3S$—$C_6H_4$ | $Q_4$ |
| 9 | $NCH_3$ | $CH_2$ | H | 4-$CF_3O$—$C_6H_4$ | $Q_4$ |
| 10 | $NCH_3$ | $CH_2$ | H | 2,4-2Cl—$C_6H_3$ | $Q_4$ |
| 11 | $NCH(CH_3)_2$ | $CH_2$ | H | 4-Cl—$C_6H_4$ | $Q_4$ |
| 12 | $NCH_3$ | $CH_2$ | H | 4-$CH_3O$—$C_6H_4$ | $Q_4$ |
| 13 | $NCH_3$ | $CH_2$ | H | 2-Cl-4-F—$C_6H_3$ | $Q_4$ |
| 14 | $NCH_3$ | $CH_2$ | H | 3-Cl—$C_6H_4$ | $Q_4$ |
| 15 | $NCH_3$ | $CH_2$ | H | 4-Br—$C_6H_4$ | $Q_4$ |
| 16 | $NCH_3$ | $CH_2$ | H | 4-$CH_3$—$C_6H_4$ | $Q_4$ |
| 17 | $NCH_3$ | $CH_2$ | H | 4-$C_2H_5$—$C_6H_4$ | $Q_4$ |
| 18 | $NCH_3$ | $CH_2$ | H | 4-$CF_3CH_2O$—$C_6H_4$ | $Q_4$ |
| 19 | $NCH_3$ | $CH_2$ | H | 4-PhO—$C_6H_4$ | $Q_4$ |
| 20 | $NCH_3$ | $CH_2$ | H | 2-Cl—$C_6H_4$ | $Q_4$ |
| 21 | $NCH_3$ | $CH_2$ | H | 6-Cl-Pyridin-3-yl | $Q_4$ |
| 22 | $NCH_3$ | $CH_2$ | H | 6-F-Pyridin-3-yl | $Q_4$ |
| 23 | $NCH_3$ | $CH_2$ | H | 6-$CF_3O$-Pyridin-3-yl | $Q_4$ |
| 24 | $NCH_3$ | $CH_2$ | H | 6-$CF_3$-Pyridin-3-yl | $Q_4$ |
| 25 | $NCH_3$ | $CH_2$ | H | 6-$CH_3O$-Pyridin-3-yl | $Q_4$ |
| 26 | $NCH_3$ | $CH_2$ | H | 6-$CF_3CH_2O$-Pyridin-3-yl | $Q_4$ |
| 27 | $NCH_3$ | $CH_2$ | H | 4-(4-Cl—Ph)—$C_6H_4$ | $Q_4$ |
| 28 | $NCH_3$ | $CH_2$ | H | Thiophen-2-yl | $Q_4$ |
| 29 | $NCH_3$ | $CH_2$ | H | 5-Cl-Thiophen-2-yl | $Q_4$ |
| 30 | $NCH_3$ | $CH_2$ | H | Thiazol-2-yl | $Q_4$ |
| 31 | $NCH_3$ | $CH_2$ | H | Furan-2-yl | $Q_4$ |
| 32 | $NCH_3$ | $CH_2$ | Cl | $C_6H_5$ | $Q_4$ |
| 33 | $NCH_3$ | $CH_2$ | Cl | 4-Cl—$C_6H_4$ | $Q_4$ |
| 34 | $NCH_3$ | $CH_2$ | Cl | 4-F—$C_6H_4$ | $Q_4$ |
| 35 | $NCH_3$ | $CH_2$ | Cl | 4-$NO_2$—$C_6H_4$ | $Q_4$ |
| 36 | $NCH_3$ | $CH_2$ | Cl | 4-$CF_3$—$C_6H_4$ | $Q_4$ |
| 37 | $NCH_3$ | $CH_2$ | Cl | 4-CN—$C_6H_4$ | $Q_4$ |
| 38 | $NCH_3$ | $CH_2$ | Cl | 4-$CH_3CO_2$—$C_6H_4$ | $Q_4$ |
| 39 | $NCH_3$ | $CH_2$ | Cl | 4-$CH_3S$—$C_6H_4$ | $Q_4$ |
| 40 | $NCH_3$ | $CH_2$ | Cl | 4-$CF_3O$—$C_6H_4$ | $Q_4$ |
| 41 | $NCH_3$ | $CH_2$ | Cl | 2,4-2Cl—$C_6H_3$ | $Q_4$ |
| 42 | $NCH(CH_3)_2$ | $CH_2$ | Cl | 4-Cl—$C_6H_4$ | $Q_4$ |
| 43 | $NCH_3$ | $CH_2$ | Cl | 4-$CH_3O$—$C_6H_4$ | $Q_4$ |
| 44 | $NCH_3$ | $CH_2$ | Cl | 2-Cl-4-F—$C_6H_3$ | $Q_4$ |
| 45 | $NCH_3$ | $CH_2$ | Cl | 3-Cl—$C_6H_4$ | $Q_4$ |
| 46 | $NCH_3$ | $CH_2$ | Cl | 4-Br—$C_6H_4$ | $Q_4$ |
| 47 | $NCH_3$ | $CH_2$ | Cl | 4-$CH_3$—$C_6H_4$ | $Q_4$ |
| 48 | $NCH_3$ | $CH_2$ | Cl | 4-$C_2H_5$—$C_6H_4$ | $Q_4$ |
| 49 | $NCH_3$ | $CH_2$ | Cl | 4-$CF_3CH_2O$—$C_6H_4$ | $Q_4$ |
| 50 | $NCH_3$ | $CH_2$ | Cl | 4-PhO—$C_6H_4$ | $Q_4$ |
| 51 | $NCH_3$ | $CH_2$ | Cl | 2-Cl—$C_6H_4$ | $Q_4$ |
| 52 | $NCH_3$ | $CH_2$ | Cl | 6-Cl-Pyridin-3-yl | $Q_4$ |
| 53 | $NCH_3$ | $CH_2$ | Cl | 6-F-Pyridin-3-yl | $Q_4$ |
| 54 | $NCH_3$ | $CH_2$ | Cl | 6-$CF_3O$-Pyridin-3-yl | $Q_4$ |
| 55 | $NCH_3$ | $CH_2$ | Cl | 6-$CF_3$-Pyridin-3-yl | $Q_4$ |
| 56 | $NCH_3$ | $CH_2$ | Cl | 6-$CH_3O$-Pyridin-3-yl | $Q_4$ |
| 57 | $NCH_3$ | $CH_2$ | Cl | 6-$CF_3CH_2O$-Pyridin-3-yl | $Q_4$ |
| 58 | $NCH_3$ | $CH_2$ | Cl | 4-(4-Cl—Ph)—$C_6H_4$ | $Q_4$ |
| 59 | $NCH_3$ | $CH_2$ | Cl | Thiophen-2-yl | $Q_4$ |
| 60 | $NCH_3$ | $CH_2$ | Cl | 5-Cl-Thiophen-2-yl | $Q_4$ |
| 61 | $NCH_3$ | $CH_2$ | Cl | Thiazol-2-yl | $Q_4$ |
| 62 | $NCH_3$ | $CH_2$ | Cl | Furan-2-yl | $Q_4$ |
| 63 | $NCH_3$ | $CH_2$ | $CH_3$ | $C_6H_5$ | $Q_4$ |
| 64 | $NCH_3$ | $CH_2$ | $CH_3$ | 4-Cl—$C_6H_4$ | $Q_4$ |
| 65 | $NCH_3$ | $CH_2$ | $CH_3$ | 4-F—$C_6H_4$ | $Q_4$ |
| 66 | $NCH_3$ | $CH_2$ | $CH_3$ | 4-$NO_2$—$C_6H_4$ | $Q_4$ |
| 67 | $NCH_3$ | $CH_2$ | $CH_3$ | 4-$CF_3$—$C_6H_4$ | $Q_4$ |
| 68 | $NCH_3$ | $CH_2$ | $CH_3$ | 4-CN—$C_6H_4$ | $Q_4$ |
| 69 | $NCH_3$ | $CH_2$ | $CH_3$ | 4-$CH_3CO_2$—$C_6H_4$ | $Q_4$ |
| 70 | $NCH_3$ | $CH_2$ | $CH_3$ | 4-$CH_3S$—$C_6H_4$ | $Q_4$ |
| 71 | $NCH_3$ | $CH_2$ | $CH_3$ | 4-$CF_3O$—$C_6H_4$ | $Q_4$ |
| 72 | $NCH_3$ | $CH_2$ | $CH_3$ | 2,4-2Cl—$C_6H_3$ | $Q_4$ |
| 73 | $NCH(CH_3)_2$ | $CH_2$ | $CH_3$ | 4-Cl—$C_6H_4$ | $Q_4$ |
| 74 | $NCH_3$ | $CH_2$ | $CH_3$ | 4-$CH_3O$—$C_6H_4$ | $Q_4$ |
| 75 | $NCH_3$ | $CH_2$ | $CH_3$ | 2-Cl-4-F—$C_6H_3$ | $Q_4$ |
| 76 | $NCH_3$ | $CH_2$ | $CH_3$ | 3-Cl—$C_6H_4$ | $Q_4$ |
| 77 | $NCH_3$ | $CH_2$ | $CH_3$ | 4-Br—$C_6H_4$ | $Q_4$ |
| 78 | $NCH_3$ | $CH_2$ | $CH_3$ | 4-$CH_3$—$C_6H_4$ | $Q_4$ |
| 79 | $NCH_3$ | $CH_2$ | $CH_3$ | 4-$C_2H_5$—$C_6H_4$ | $Q_4$ |
| 80 | $NCH_3$ | $CH_2$ | $CH_3$ | 4-$CF_3CH_2O$—$C_6H_4$ | $Q_4$ |
| 81 | $NCH_3$ | $CH_2$ | $CH_3$ | 4-PhO—$C_6H_4$ | $Q_4$ |
| 82 | $NCH_3$ | $CH_2$ | $CH_3$ | 2-Cl—$C_6H_4$ | $Q_4$ |
| 83 | $NCH_3$ | $CH_2$ | $CH_3$ | 6-Cl-Pyridin-3-yl | $Q_4$ |
| 84 | $NCH_3$ | $CH_2$ | $CH_3$ | 6-F-Pyridin-3-yl | $Q_4$ |
| 85 | $NCH_3$ | $CH_2$ | $CH_3$ | 6-$CF_3O$-Pyridin-3-yl | $Q_4$ |
| 86 | $NCH_3$ | $CH_2$ | $CH_3$ | 6-$CF_3$-Pyridin-3-yl | $Q_4$ |
| 87 | $NCH_3$ | $CH_2$ | $CH_3$ | 6-$CH_3O$-Pyridin-3-yl | $Q_4$ |
| 88 | $NCH_3$ | $CH_2$ | $CH_3$ | 6-$CF_3CH_2O$-Pyridin-3-yl | $Q_4$ |
| 89 | $NCH_3$ | $CH_2$ | $CH_3$ | 4-(4-Cl—Ph)—$C_6H_4$ | $Q_4$ |
| 90 | $NCH_3$ | $CH_2$ | $CH_3$ | Thiophen-2-yl | $Q_4$ |
| 91 | $NCH_3$ | $CH_2$ | $CH_3$ | 5-Cl-Thiophen-2-yl | $Q_4$ |
| 92 | $NCH_3$ | $CH_2$ | $CH_3$ | Thiazol-2-yl | $Q_4$ |
| 93 | $NCH_3$ | $CH_2$ | $CH_3$ | Furan-2-yl | $Q_4$ |
| 94 | O | $CH_2$ | H | $C_6H_5$ | $Q_4$ |
| 95 | O | $CH_2$ | H | 4-Cl—$C_6H_4$ | $Q_4$ |
| 96 | O | $CH_2$ | H | 4-F—$C_6H_4$ | $Q_4$ |
| 97 | O | $CH_2$ | H | 4-$NO_2$—$C_6H_4$ | $Q_4$ |
| 98 | O | $CH_2$ | H | 4-$CF_3$—$C_6H_4$ | $Q_4$ |
| 99 | O | $CH_2$ | H | 4-CN—$C_6H_4$ | $Q_4$ |
| 100 | O | $CH_2$ | H | 4-$CH_3CO_2$—$C_6H_4$ | $Q_4$ |
| 101 | O | $CH_2$ | H | 4-$CH_3S$—$C_6H_4$ | $Q_4$ |
| 102 | O | $CH_2$ | H | 4-$CF_3O$—$C_6H_4$ | $Q_4$ |
| 103 | O | $CH_2$ | H | 2,4-2Cl—$C_6H_3$ | $Q_4$ |
| 104 | O | $CH_2$ | H | 4-$CH_3O$—$C_6H_4$ | $Q_4$ |
| 105 | O | $CH_2$ | H | 2-Cl-4-F—$C_6H_3$ | $Q_4$ |
| 106 | O | $CH_2$ | H | 3-Cl—$C_6H_4$ | $Q_4$ |
| 107 | O | $CH_2$ | H | 4-$CH_3$—$C_6H_4$ | $Q_4$ |
| 108 | O | $CH_2$ | H | 4-Br—$C_6H_4$ | $Q_4$ |
| 109 | O | $CH_2$ | H | 4-$C_2H_5$—$C_6H_4$ | $Q_4$ |
| 110 | O | $CH_2$ | H | 4-$CF_3CH_2O$—$C_6H_4$ | $Q_4$ |
| 111 | O | $CH_2$ | H | 4-PhO—$C_6H_4$ | $Q_4$ |
| 112 | O | $CH_2$ | H | 2-Cl—$C_6H_4$ | $Q_4$ |
| 113 | O | $CH_2$ | H | 6-Cl-Pyridin-3-yl | $Q_4$ |
| 114 | O | $CH_2$ | H | 6-F-Pyridin-3-yl | $Q_4$ |
| 115 | O | $CH_2$ | H | 6-$CF_3O$-Pyridin-3-yl | $Q_4$ |
| 116 | O | $CH_2$ | H | 6-$CF_3$-Pyridin-3-yl | $Q_4$ |
| 117 | O | $CH_2$ | H | 6-$CH_3O$-Pyridin-3-yl | $Q_4$ |

TABLE 1-continued

I

| number | X₁ | X₂ | R₁ | Ar | Q |
|---|---|---|---|---|---|
| 118 | O | CH₂ | H | 6-CF₃CH₂O-Pyridin-3-yl | Q₄ |
| 119 | O | CH₂ | H | 4-(4-Cl—Ph)—C₆H₄ | Q₄ |
| 120 | O | CH₂ | H | Thiophen-2-yl | Q₄ |
| 121 | O | CH₂ | H | 5-Cl-Thiophen-2-yl | Q₄ |
| 122 | O | CH₂ | H | Thiazol-2-yl | Q₄ |
| 123 | O | CH₂ | H | Furan-2-yl | Q₄ |
| 124 | O | CH₂ | Cl | C₆H₅ | Q₄ |
| 125 | O | CH₂ | Cl | 4-Cl—C₆H₄ | Q₄ |
| 126 | O | CH₂ | Cl | 4-F—C₆H₄ | Q₄ |
| 127 | O | CH₂ | Cl | 4-NO₂—C₆H₄ | Q₄ |
| 128 | O | CH₂ | Cl | 4-CF₃—C₆H₄ | Q₄ |
| 129 | O | CH₂ | Cl | 4-CN—C₆H₄ | Q₄ |
| 130 | O | CH₂ | Cl | 4-CH₃CO₂—C₆H₄ | Q₄ |
| 131 | O | CH₂ | Cl | 4-CH₃S—C₆H₄ | Q₄ |
| 132 | O | CH₂ | Cl | 4-CF₃O—C₆H₄ | Q₄ |
| 133 | O | CH₂ | Cl | 2,4-2Cl—C₆H₃ | Q₄ |
| 134 | O | CH₂ | Cl | 4-CH₃O—C₆H₄ | Q₄ |
| 135 | O | CH₂ | Cl | 2-Cl-4-F—C₆H₃ | Q₄ |
| 136 | O | CH₂ | Cl | 3-Cl—C₆H₄ | Q₄ |
| 137 | O | CH₂ | Cl | 4-CH₃—C₆H₄ | Q₄ |
| 138 | O | CH₂ | Cl | 4-Br—C₆H₄ | Q₄ |
| 139 | O | CH₂ | Cl | 4-C₂H₅—C₆H₄ | Q₄ |
| 140 | O | CH₂ | Cl | 4-CF₃CH₂O—C₆H₄ | Q₄ |
| 141 | O | CH₂ | Cl | 4-PhO—C₆H₄ | Q₄ |
| 142 | O | CH₂ | Cl | 2-Cl—C₆H₄ | Q₄ |
| 143 | O | CH₂ | Cl | 6-Cl-Pyridin-3-yl | Q₄ |
| 144 | O | CH₂ | Cl | 6-F-Pyridin-3-yl | Q₄ |
| 145 | O | CH₂ | Cl | 6-CF₃O-Pyridin-3-yl | Q₄ |
| 146 | O | CH₂ | Cl | 6-CF₃-Pyridin-3-yl | Q₄ |
| 147 | O | CH₂ | Cl | 6-CH₃O-Pyridin-3-yl | Q₄ |
| 148 | O | CH₂ | Cl | 6-CF₃CH₂O-Pyridin-3-yl | Q₄ |
| 149 | O | CH₂ | Cl | 4-(4-Cl—Ph)—C₆H₄ | Q₄ |
| 150 | O | CH₂ | Cl | Thiophen-2-yl | Q₄ |
| 151 | O | CH₂ | Cl | 5-Cl-Thiophen-2-yl | Q₄ |
| 152 | O | CH₂ | Cl | Thiazol-2-yl | Q₄ |
| 153 | O | CH₂ | Cl | Furan-2-yl | Q₄ |
| 154 | O | CH₂ | CH₃ | C₆H₅ | Q₄ |
| 155 | O | CH₂ | CH₃ | 4-Cl—C₆H₄ | Q₄ |
| 156 | O | CH₂ | CH₃ | 4-F—C₆H₄ | Q₄ |
| 157 | O | CH₂ | CH₃ | 4-NO₂—C₆H₄ | Q₄ |
| 158 | O | CH₂ | CH₃ | 4-CF₃—C₆H₄ | Q₄ |
| 159 | O | CH₂ | CH₃ | 4-CN—C₆H₄ | Q₄ |
| 160 | O | CH₂ | CH₃ | 4-CH₃CO₂—C₆H₄ | Q₄ |
| 161 | O | CH₂ | CH₃ | 4-CH₃S—C₆H₄ | Q₄ |
| 162 | O | CH₂ | CH₃ | 4-CF₃O—C₆H₄ | Q₄ |
| 163 | O | CH₂ | CH₃ | 2,4-2Cl—C₆H₃ | Q₄ |
| 164 | O | CH₂ | CH₃ | 4-CH₃O—C₆H₄ | Q₄ |
| 165 | O | CH₂ | CH₃ | 2-Cl-4-F—C₆H₃ | Q₄ |
| 166 | O | CH₂ | CH₃ | 3-Cl—C₆H₄ | Q₄ |
| 167 | O | CH₂ | CH₃ | 4-CH₃—C₆H₄ | Q₄ |
| 168 | O | CH₂ | CH₃ | 4-Br—C₆H₄ | Q₄ |
| 169 | O | CH₂ | CH₃ | 4-C₂H₅—C₆H₄ | Q₄ |
| 170 | O | CH₂ | CH₃ | 4-CF₃CH₂O—C₆H₄ | Q₄ |
| 171 | O | CH₂ | CH₃ | 4-PhO—C₆H₄ | Q₄ |
| 172 | O | CH₂ | CH₃ | 2-Cl—C₆H₄ | Q₄ |
| 173 | O | CH₂ | CH₃ | 6-Cl-Pyridin-3-yl | Q₄ |
| 174 | O | CH₂ | CH₃ | 6-F-Pyridin-3-yl | Q₄ |
| 175 | O | CH₂ | CH₃ | 6-CF₃O-Pyridin-3-yl | Q₄ |
| 176 | O | CH₂ | CH₃ | 6-CF₃-Pyridin-3-yl | Q₄ |
| 177 | O | CH₂ | CH₃ | 6-CH₃O-Pyridin-3-yl | Q₄ |
| 178 | O | CH₂ | CH₃ | 6-CF₃CH₂O-Pyridin-3-yl | Q₄ |
| 179 | O | CH₂ | CH₃ | 4-(4-Cl—Ph)—C₆H₄ | Q₄ |
| 180 | O | CH₂ | CH₃ | Thiophen-2-yl | Q₄ |
| 181 | O | CH₂ | CH₃ | 5-Cl-Thiophen-2-yl | Q₄ |
| 182 | O | CH₂ | CH₃ | Thiazol-2-yl | Q₄ |
| 183 | O | CH₂ | CH₃ | Furan-2-yl | Q₄ |
| 184 | NCH₃ | M | H | C₆H₅ | Q₁ |
| 185 | NCH₃ | M | H | 4-Cl—C₆H₄ | Q₁ |
| 186 | NCH₃ | M | H | 4-F—C₆H₄ | Q₁ |
| 187 | NCH₃ | M | H | 4-NO₂—C₆H₄ | Q₁ |
| 188 | NCH₃ | M | H | 4-CF₃—C₆H₄ | Q₁ |
| 189 | NCH₃ | M | H | 4-CN—C₆H₄ | Q₁ |
| 190 | NCH₃ | M | H | 4-CH₃CO₂—C₆H₄ | Q₁ |
| 191 | NCH₃ | M | H | 4-CH₃S—C₆H₄ | Q₁ |
| 192 | NCH₃ | M | H | 4-CF₃O—C₆H₄ | Q₁ |
| 193 | NCH₃ | M | H | 2,4-2Cl—C₆H₃ | Q₁ |
| 194 | NCH(CH₃)₂ | M | H | 4-Cl—C₆H₄ | Q₁ |
| 195 | NCH₃ | M | H | 4-CH₃O—C₆H₄ | Q₁ |
| 196 | NCH₃ | M | H | 2-Cl-4-F—C₆H₃ | Q₁ |
| 197 | NCH₃ | M | H | 3-Cl—C₆H₄ | Q₁ |
| 198 | NCH₃ | M | H | 4-Br—C₆H₄ | Q₁ |
| 199 | NCH₃ | M | H | 4-CH₃—C₆H₄ | Q₁ |
| 200 | NCH₃ | M | H | 4-C₂H₅—C₆H₄ | Q₁ |
| 201 | NCH₃ | M | H | 4-CF₃CH₂O—C₆H₄ | Q₁ |
| 202 | NCH₃ | M | H | 4-PhO—C₆H₄ | Q₁ |
| 203 | NCH₃ | M | H | 2-Cl—C₆H₄ | Q₁ |
| 204 | NCH₃ | M | H | 6-Cl-Pyridin-3-yl | Q₁ |
| 205 | NCH₃ | M | H | 6-F-Pyridin-3-yl | Q₁ |
| 206 | NCH₃ | M | H | 6-CF₃O-Pyridin-3-yl | Q₁ |
| 207 | NCH₃ | M | H | 6-CF₃-Pyridin-3-yl | Q₁ |
| 208 | NCH₃ | M | H | 6-CH₃O-Pyridin-3-yl | Q₁ |
| 209 | NCH₃ | M | H | 6-CF₃CH₂O-Pyridin-3-yl | Q₁ |
| 210 | NCH₃ | M | H | 4-(4-Cl—Ph)—C₆H₄ | Q₁ |
| 211 | NCH₃ | M | H | Thiophen-2-yl | Q₁ |
| 212 | NCH₃ | M | H | 5-Cl-Thiophen-2-yl | Q₁ |
| 213 | NCH₃ | M | H | Thiazol-2-yl | Q₁ |
| 214 | NCH₃ | M | H | Furan-2-yl | Q₁ |
| 215 | NCH₃ | M | Cl | C₆H₅ | Q₁ |
| 216 | NCH₃ | M | Cl | 4-Cl—C₆H₄ | Q₁ |
| 217 | NCH₃ | M | Cl | 4-F—C₆H₄ | Q₁ |
| 218 | NCH₃ | M | Cl | 4-NO₂—C₆H₄ | Q₁ |
| 219 | NCH₃ | M | Cl | 4-CF₃—C₆H₄ | Q₁ |
| 220 | NCH₃ | M | Cl | 4-CN—C₆H₄ | Q₁ |
| 221 | NCH₃ | M | Cl | 4-CH₃CO₂—C₆H₄ | Q₁ |
| 222 | NCH₃ | M | Cl | 4-CH₃S—C₆H₄ | Q₁ |
| 223 | NCH₃ | M | Cl | 4-CF₃O—C₆H₄ | Q₁ |
| 224 | NCH₃ | M | Cl | 2,4-2Cl—C₆H₃ | Q₁ |
| 225 | NCH(CH₃)₂ | M | Cl | 4-Cl—C₆H₄ | Q₁ |
| 226 | NCH₃ | M | Cl | 4-CH₃O—C₆H₄ | Q₁ |
| 227 | NCH₃ | M | Cl | 2-Cl-4-F—C₆H₃ | Q₁ |
| 228 | NCH₃ | M | Cl | 3-Cl—C₆H₄ | Q₁ |
| 229 | NCH₃ | M | Cl | 4-Br—C₆H₄ | Q₁ |
| 230 | NCH₃ | M | Cl | 4-CH₃—C₆H₄ | Q₁ |
| 231 | NCH₃ | M | Cl | 4-C₂H₅—C₆H₄ | Q₁ |
| 232 | NCH₃ | M | Cl | 4-CF₃CH₂O—C₆H₄ | Q₁ |
| 233 | NCH₃ | M | Cl | 4-PhO—C₆H₄ | Q₁ |
| 234 | NCH₃ | M | Cl | 2-Cl—C₆H₄ | Q₁ |
| 235 | NCH₃ | M | Cl | 6-Cl-Pyridin-3-yl | Q₁ |
| 236 | NCH₃ | M | Cl | 6-F-Pyridin-3-yl | Q₁ |
| 237 | NCH₃ | M | Cl | 6-CF₃O-Pyridin-3-yl | Q₁ |
| 238 | NCH₃ | M | Cl | 6-CF₃-Pyridin-3-yl | Q₁ |
| 239 | NCH₃ | M | Cl | 6-CH₃O-Pyridin-3-yl | Q₁ |
| 240 | NCH₃ | M | Cl | 6-CF₃CH₂O-Pyridin-3-yl | Q₁ |
| 241 | NCH₃ | M | Cl | 4-(4-Cl—Ph)—C₆H₄ | Q₁ |
| 242 | NCH₃ | M | Cl | Thiophen-2-yl | Q₁ |
| 243 | NCH₃ | M | Cl | 5-Cl-Thiophen-2-yl | Q₁ |
| 244 | NCH₃ | M | Cl | Thiazol-2-yl | Q₁ |
| 245 | NCH₃ | M | Cl | Furan-2-yl | Q₁ |
| 246 | NCH₃ | M | CH₃ | C₆H₅ | Q₁ |
| 247 | NCH₃ | M | CH₃ | 4-Cl—C₆H₄ | Q₁ |
| 248 | NCH₃ | M | CH₃ | 4-F—C₆H₄ | Q₁ |
| 249 | NCH₃ | M | CH₃ | 4-NO₂—C₆H₄ | Q₁ |
| 250 | NCH₃ | M | CH₃ | 4-CF₃—C₆H₄ | Q₁ |
| 251 | NCH₃ | M | CH₃ | 4-CN—C₆H₄ | Q₁ |

TABLE 1-continued

I

![Structure I: Ar-substituted pyrazole with R1, X1, X2, O-phenyl-Q](structure)

| number | X₁ | X₂ | R₁ | Ar | Q |
|---|---|---|---|---|---|
| 252 | NCH₃ | M | CH₃ | 4-CH₃CO₂—C₆H₄ | Q₁ |
| 253 | NCH₃ | M | CH₃ | 4-CH₃S—C₆H₄ | Q₁ |
| 254 | NCH₃ | M | CH₃ | 4-CF₃O—C₆H₄ | Q₁ |
| 255 | NCH₃ | M | CH₃ | 2,4-2Cl—C₆H₃ | Q₁ |
| 256 | NCH(CH₃)₂ | M | CH₃ | 4-Cl—C₆H₄ | Q₁ |
| 257 | NCH₃ | M | CH₃ | 4-CH₃O—C₆H₄ | Q₁ |
| 258 | NCH₃ | M | CH₃ | 2-Cl-4-F—C₆H₃ | Q₁ |
| 259 | NCH₃ | M | CH₃ | 3-Cl—C₆H₄ | Q₁ |
| 260 | NCH₃ | M | CH₃ | 4-Br—C₆H₄ | Q₁ |
| 261 | NCH₃ | M | CH₃ | 4-CH₃—C₆H₄ | Q₁ |
| 262 | NCH₃ | M | CH₃ | 4-C₂H₅—C₆H₄ | Q₁ |
| 263 | NCH₃ | M | CH₃ | 4-CF₃CH₂O—C₆H₄ | Q₁ |
| 264 | NCH₃ | M | CH₃ | 4-PhO—C₆H₄ | Q₁ |
| 265 | NCH₃ | M | CH₃ | 2-Cl—C₆H₄ | Q₁ |
| 266 | NCH₃ | M | CH₃ | 6-Cl-Pyridin-3-yl | Q₁ |
| 267 | NCH₃ | M | CH₃ | 6-F-Pyridin-3-yl | Q₁ |
| 268 | NCH₃ | M | CH₃ | 6-CF₃O-Pyridin-3-yl | Q₁ |
| 269 | NCH₃ | M | CH₃ | 6-CF₃-Pyridin-3-yl | Q₁ |
| 270 | NCH₃ | M | CH₃ | 6-CH₃O-Pyridin-3-yl | Q₁ |
| 271 | NCH₃ | M | CH₃ | 6-CF₃CH₂O-Pyridin-3-yl | Q₁ |
| 272 | NCH₃ | M | CH₃ | 4-(4-Cl—Ph)—C₆H₄ | Q₁ |
| 273 | NCH₃ | M | CH₃ | Thiophen-2-yl | Q₁ |
| 274 | NCH₃ | M | CH₃ | 5-Cl-Thiophen-2-yl | Q₁ |
| 275 | NCH₃ | M | CH₃ | Thiazol-2-yl | Q₁ |
| 276 | NCH₃ | M | CH₃ | Furan-2-yl | Q₁ |
| 277 | O | M | H | C₆H₅ | Q₁ |
| 278 | O | M | H | 4-Cl—C₆H₄ | Q₁ |
| 279 | O | M | H | 4-F—C₆H₄ | Q₁ |
| 280 | O | M | H | 4-NO₂—C₆H₄ | Q₁ |
| 281 | O | M | H | 4-CF₃—C₆H₄ | Q₁ |
| 282 | O | M | H | 4-CN—C₆H₄ | Q₁ |
| 283 | O | M | H | 4-CH₃CO₂—C₆H₄ | Q₁ |
| 284 | O | M | H | 4-CH₃S—C₆H₄ | Q₁ |
| 285 | O | M | H | 4-CF₃O—C₆H₄ | Q₁ |
| 286 | O | M | H | 2,4-2Cl—C₆H₃ | Q₁ |
| 287 | O | M | H | 4-CH₃O—C₆H₄ | Q₁ |
| 288 | O | M | H | 2-Cl-4-F—C₆H₃ | Q₁ |
| 289 | O | M | H | 3-Cl—C₆H₄ | Q₁ |
| 290 | O | M | H | 4-Br—C₆H₄ | Q₁ |
| 291 | O | M | H | 4-CH₃—C₆H₄ | Q₁ |
| 292 | O | M | H | 4-C₂H₅—C₆H₄ | Q₁ |
| 293 | O | M | H | 4-CF₃CH₂O—C₆H₄ | Q₁ |
| 294 | O | M | H | 4-PhO—C₆H₄ | Q₁ |
| 295 | O | M | H | 2-Cl—C₆H₄ | Q₁ |
| 296 | O | M | H | 6-Cl-Pyridin-3-yl | Q₁ |
| 297 | O | M | H | 6-F-Pyridin-3-yl | Q₁ |
| 298 | O | M | H | 6-CF₃O-Pyridin-3-yl | Q₁ |
| 299 | O | M | H | 6-CF₃-Pyridin-3-yl | Q₁ |
| 300 | O | M | H | 6-CH₃O-Pyridin-3-yl | Q₁ |
| 301 | O | M | H | 6-CF₃CH₂O-Pyridin-3-yl | Q₁ |
| 302 | O | M | H | 4-(4-Cl—Ph)—C₆H₄ | Q₁ |
| 303 | O | M | H | Thiophen-2-yl | Q₁ |
| 304 | O | M | H | 5-Cl-Thiophen-2-yl | Q₁ |
| 305 | O | M | H | Thiazol-2-yl | Q₁ |
| 306 | O | M | H | Furan-2-yl | Q₁ |
| 307 | O | M | Cl | C₆H₅ | Q₁ |
| 308 | O | M | Cl | 4-Cl—C₆H₄ | Q₁ |
| 309 | O | M | Cl | 4-F—C₆H₄ | Q₁ |
| 310 | O | M | Cl | 4-NO₂—C₆H₄ | Q₁ |
| 311 | O | M | Cl | 4-CF₃—C₆H₄ | Q₁ |
| 312 | O | M | Cl | 4-CN—C₆H₄ | Q₁ |
| 313 | O | M | Cl | 4-CH₃CO₂—C₆H₄ | Q₁ |
| 314 | O | M | Cl | 4-CH₃S—C₆H₄ | Q₁ |
| 315 | O | M | Cl | 4-CF₃O—C₆H₄ | Q₁ |
| 316 | O | M | Cl | 2,4-2Cl—C₆H₃ | Q₁ |
| 317 | O | M | Cl | 4-CH₃O—C₆H₄ | Q₁ |
| 318 | O | M | Cl | 2-Cl-4-F—C₆H₃ | Q₁ |
| 319 | O | M | Cl | 3-Cl—C₆H₄ | Q₁ |
| 320 | O | M | Cl | 4-Br—C₆H₄ | Q₁ |
| 321 | O | M | Cl | 4-CH₃—C₆H₄ | Q₁ |
| 322 | O | M | Cl | 4-C₂H₅—C₆H₄ | Q₁ |
| 323 | O | M | Cl | 4-CF₃CH₂O—C₆H₄ | Q₁ |
| 324 | O | M | Cl | 4-PhO—C₆H₄ | Q₁ |
| 325 | O | M | Cl | 2-Cl—C₆H₄ | Q₁ |
| 326 | O | M | Cl | 6-Cl-Pyridin-3-yl | Q₁ |
| 327 | O | M | Cl | 6-F-Pyridin-3-yl | Q₁ |
| 328 | O | M | Cl | 6-CF₃O-Pyridin-3-yl | Q₁ |
| 329 | O | M | Cl | 6-CF₃-Pyridin-3-yl | Q₁ |
| 330 | O | M | Cl | 6-CH₃O-Pyridin-3-yl | Q₁ |
| 331 | O | M | Cl | 6-CF₃CH₂O-Pyridin-3-yl | Q₁ |
| 332 | O | M | Cl | 4-(4-Cl—Ph)—C₆H₄ | Q₁ |
| 333 | O | M | Cl | Thiophen-2-yl | Q₁ |
| 334 | O | M | Cl | 5-Cl-Thiophen-2-yl | Q₁ |
| 335 | O | M | Cl | Thiazol-2-yl | Q₁ |
| 336 | O | M | Cl | Furan-2-yl | Q₁ |
| 337 | O | M | CH₃ | C₆H₅ | Q₁ |
| 338 | O | M | CH₃ | 4-Cl—C₆H₄ | Q₁ |
| 339 | O | M | CH₃ | 4-F—C₆H₄ | Q₁ |
| 340 | O | M | CH₃ | 4-NO₂—C₆H₄ | Q₁ |
| 341 | O | M | CH₃ | 4-CF₃—C₆H₄ | Q₁ |
| 342 | O | M | CH₃ | 4-CN—C₆H₄ | Q₁ |
| 343 | O | M | CH₃ | 4-CH₃CO₂—C₆H₄ | Q₁ |
| 344 | O | M | CH₃ | 4-CH₃S—C₆H₄ | Q₁ |
| 345 | O | M | CH₃ | 4-CF₃O—C₆H₄ | Q₁ |
| 346 | O | M | CH₃ | 2,4-2Cl—C₆H₃ | Q₁ |
| 347 | O | M | CH₃ | 4-CH₃O—C₆H₄ | Q₁ |
| 348 | O | M | CH₃ | 2-Cl-4-F—C₆H₃ | Q₁ |
| 349 | O | M | CH₃ | 3-Cl—C₆H₄ | Q₁ |
| 350 | O | M | CH₃ | 4-Br—C₆H₄ | Q₁ |
| 351 | O | M | CH₃ | 4-CH₃—C₆H₄ | Q₁ |
| 352 | O | M | CH₃ | 4-C₂H₅—C₆H₄ | Q₁ |
| 353 | O | M | CH₃ | 4-CF₃CH₂O—C₆H₄ | Q₁ |
| 354 | O | M | CH₃ | 4-PhO—C₆H₄ | Q₁ |
| 355 | O | M | CH₃ | 2-Cl—C₆H₄ | Q₁ |
| 356 | O | M | CH₃ | 6-Cl-Pyridin-3-yl | Q₁ |
| 357 | O | M | CH₃ | 6-F-Pyridin-3-yl | Q₁ |
| 358 | O | M | CH₃ | 6-CF₃O-Pyridin-3-yl | Q₁ |
| 359 | O | M | CH₃ | 6-CF₃-Pyridin-3-yl | Q₁ |
| 360 | O | M | CH₃ | 6-CH₃O-Pyridin-3-yl | Q₁ |
| 361 | O | M | CH₃ | 6-CF₃CH₂O-Pyridin-3-yl | Q₁ |
| 362 | O | M | CH₃ | 4-(4-Cl—Ph)—C₆H₄ | Q₁ |
| 363 | O | M | CH₃ | Thiophen-2-yl | Q₁ |
| 364 | O | M | CH₃ | 5-Cl-Thiophen-2-yl | Q₁ |
| 365 | O | M | CH₃ | Thiazol-2-yl | Q₁ |
| 366 | O | M | CH₃ | Furan-2-yl | Q₁ |
| 367 | NCH₃ | CH₂ | H | Thiophen-2-yl | Q₁ |
| 368 | NCH₃ | CH₂ | H | 5-Cl-Thiophen-2-yl | Q₁ |
| 369 | NCH₃ | CH₂ | H | Thiazol-2-yl | Q₁ |
| 370 | NCH₃ | CH₂ | H | Furan-2-yl | Q₁ |
| 371 | NCH₃ | CH₂ | Cl | Thiophen-2-yl | Q₁ |
| 372 | NCH₃ | CH₂ | Cl | 5-Cl-Thiophen-2-yl | Q₁ |
| 373 | NCH₃ | CH₂ | Cl | Thiazol-2-yl | Q₁ |
| 374 | NCH₃ | CH₂ | Cl | Furan-2-yl | Q₁ |
| 375 | NCH₃ | CH₂ | CH₃ | Thiophen-2-yl | Q₁ |
| 376 | NCH₃ | CH₂ | CH₃ | 5-Cl-Thiophen-2-yl | Q₁ |
| 377 | NCH₃ | CH₂ | CH₃ | Thiazol-2-yl | Q₁ |
| 378 | NCH₃ | CH₂ | CH₃ | Furan-2-yl | Q₁ |
| 379 | O | CH₂ | H | Thiophen-2-yl | Q₁ |
| 380 | O | CH₂ | H | 5-Cl-Thiophen-2-yl | Q₁ |
| 381 | O | CH₂ | H | Thiazol-2-yl | Q₁ |
| 382 | O | CH₂ | H | Furan-2-yl | Q₁ |
| 383 | O | CH₂ | Cl | Thiophen-2-yl | Q₁ |
| 384 | O | CH₂ | Cl | 5-Cl-Thiophen-2-yl | Q₁ |
| 385 | O | CH₂ | Cl | Thiazol-2-yl | Q₁ |

TABLE 1-continued

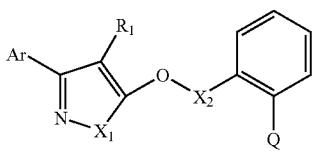

| number | X₁ | X₂ | R₁ | Ar | Q |
|---|---|---|---|---|---|
| 386 | O | CH₂ | Cl | Furan-2-yl | Q₁ |
| 387 | O | CH₂ | CH₃ | Thiophen-2-yl | Q₁ |
| 388 | O | CH₂ | CH₃ | 5-Cl-Thiophen-2-yl | Q₁ |
| 389 | O | CH₂ | CH₃ | Thiazol-2-yl | Q₁ |
| 390 | O | CH₂ | CH₃ | Furan-2-yl | Q₁ |
| 391 | NCH₃ | CH₂ | H | Thiophen-2-yl | Q₂ |
| 392 | NCH₃ | CH₂ | H | 5-Cl-Thiophen-2-yl | Q₂ |
| 393 | NCH₃ | CH₂ | H | Thiazol-2-yl | Q₂ |
| 394 | NCH₃ | CH₂ | H | Furan-2-yl | Q₂ |
| 395 | NCH₃ | CH₂ | Cl | Thiophen-2-yl | Q₂ |
| 396 | NCH₃ | CH₂ | Cl | 5-Cl-Thiophen-2-yl | Q₂ |
| 397 | NCH₃ | CH₂ | Cl | Thiazol-2-yl | Q₂ |
| 398 | NCH₃ | CH₂ | Cl | Furan-2-yl | Q₂ |
| 399 | NCH₃ | CH₂ | CH₃ | Thiophen-2-yl | Q₂ |
| 400 | NCH₃ | CH₂ | CH₃ | 5-Cl-Thiophen-2-yl | Q₂ |
| 401 | NCH₃ | CH₂ | CH₃ | Thiazol-2-yl | Q₂ |
| 402 | NCH₃ | CH₂ | CH₃ | Furan-2-yl | Q₂ |
| 403 | O | CH₂ | H | Thiophen-2-yl | Q₂ |
| 404 | O | CH₂ | H | 5-Cl-Thiophen-2-yl | Q₂ |
| 405 | O | CH₂ | H | Thiazol-2-yl | Q₂ |
| 406 | O | CH₂ | H | Furan-2-yl | Q₂ |
| 407 | O | CH₂ | Cl | Thiophen-2-yl | Q₂ |
| 408 | O | CH₂ | Cl | 5-Cl-Thiophen-2-yl | Q₂ |
| 409 | O | CH₂ | Cl | Thiazol-2-yl | Q₂ |
| 410 | O | CH₂ | Cl | Furan-2-yl | Q₂ |
| 411 | O | CH₂ | CH₃ | Thiophen-2-yl | Q₂ |
| 412 | O | CH₂ | CH₃ | 5-Cl-Thiophen-2-yl | Q₂ |
| 413 | O | CH₂ | CH₃ | Thiazol-2-yl | Q₂ |
| 414 | O | CH₂ | CH₃ | Furan-2-yl | Q₂ |
| 415 | NCH₃ | CH₂ | H | Thiophen-2-yl | Q₃ |
| 416 | NCH₃ | CH₂ | H | 5-Cl-Thiophen-2-yl | Q₃ |
| 417 | NCH₃ | CH₂ | H | Thiazol-2-yl | Q₃ |
| 418 | NCH₃ | CH₂ | H | Furan-2-yl | Q₃ |
| 419 | NCH₃ | CH₂ | Cl | Thiophen-2-yl | Q₃ |
| 420 | NCH₃ | CH₂ | Cl | 5-Cl-Thiophen-2-yl | Q₃ |
| 421 | NCH₃ | CH₂ | Cl | Thiazol-2-yl | Q₃ |
| 422 | NCH₃ | CH₂ | Cl | Furan-2-yl | Q₃ |
| 423 | NCH₃ | CH₂ | CH₃ | Thiophen-2-yl | Q₃ |
| 424 | NCH₃ | CH₂ | CH₃ | 5-Cl-Thiophen-2-yl | Q₃ |
| 425 | NCH₃ | CH₂ | CH₃ | Thiazol-2-yl | Q₃ |
| 426 | NCH₃ | CH₂ | CH₃ | Furan-2-yl | Q₃ |
| 427 | O | CH₂ | H | Thiophen-2-yl | Q₃ |
| 428 | O | CH₂ | H | 5-Cl-Thiophen-2-yl | Q₃ |
| 429 | O | CH₂ | H | Thiazol-2-yl | Q₃ |
| 430 | O | CH₂ | H | Furan-2-yl | Q₃ |
| 431 | O | CH₂ | Cl | Thiophen-2-yl | Q₃ |
| 432 | O | CH₂ | Cl | 5-Cl-Thiophen-2-yl | Q₃ |
| 433 | O | CH₂ | Cl | Thiazol-2-yl | Q₃ |
| 434 | O | CH₂ | Cl | Furan-2-yl | Q₃ |
| 435 | O | CH₂ | CH₃ | Thiophen-2-yl | Q₃ |
| 436 | O | CH₂ | CH₃ | 5-Cl-Thiophen-2-yl | Q₃ |
| 437 | O | CH₂ | CH₃ | Thiazol-2-yl | Q₃ |
| 438 | O | CH₂ | CH₃ | Furan-2-yl | Q₃ |
| 439 | NCH₃ | CH₂ | H | 2-CH₃O—C₆H₄ | Q₄ |
| 440 | NCH₃ | CH₂ | H | 2,5-2CH₃-Thiophen-3-yl | Q₄ |
| 441 | NCH₃ | CH₂ | H | 2,5-2CH₃-Thiophen-3-yl | Q₁ |
| 442 | NCH₃ | CH₂ | H | 2,5-2CH₃-Thiophen-3-yl | Q₂ |
| 443 | NCH₃ | CH₂ | H | 2,4-2CH₃—C₆H₃ | Q₄ |
| 444 | NCH₃ | CH₂ | H | 3,4-2CH₃—C₆H₃ | Q₄ |
| 445 | NCH₃ | CH₂ | H | 2,5-2CH₃—C₆H₃ | Q₄ |
| 446 | NCH₃ | CH₂ | H | 2,6-2CH₃—C₆H₃ | Q₄ |
| 447 | NCH₃ | CH₂ | CH₃ | 2,4-2CH₃—C₆H₃ | Q₄ |
| 448 | NCH₃ | CH₂ | CH₃ | 3,4-2CH₃—C₆H₃ | Q₄ |
| 449 | NCH₃ | CH₂ | CH₃ | 2,5-2CH₃—C₆H₃ | Q₄ |
| 450 | NCH₃ | CH₂ | CH₃ | 2,6-2CH₃—C₆H₃ | Q₄ |

Wherein:

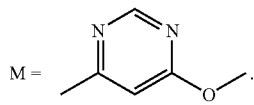

The present invention also includes preparation of the compounds having formula I.

Compounds having general formula I and their stereoisomers can be prepared by reaction of azoles compounds containing hydroxy group having general formula III with halomethylbenzene having general formula IV at the present of base:

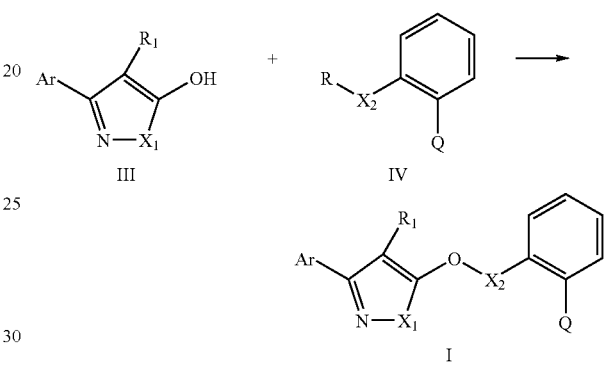

Wherein: R is leaving group, such as Cl or Br, other groups are as defined above.

The proper solvent mentioned above may be selected from tetrahydrofuran, acetonitrile, toluene, xylene, benzene, DMF, DMSO, acetone or butanone and so on.

The proper base mentioned above may be selected from potassium hydroxide, sodium hydroxide, sodium carbonate, potassium carbonate, sodium bicarbonate, triethylamine, pyridine, sodium methoxide, sodium ethoxide, sodium hydride, potassium or sodium tert-butoxide and so on.

The proper temperature mentioned above is from room temperature to boiling point of solvent, normal temperature is from 20 to 100° C.

The reaction may be finished after 30 minutes-20 hours, 1-10 hours in general.

Intermediate of the general formula III can be prepared by reaction of intermediate of the general formula II with (substituted) hydrazine or hydroxylamine according to known methods. Intermediate of the general formula II can be bought or prepared according to known methods, refer to U.S. Pat. No. 3,781,438, CN1257490, WO 9615115 and so on.

The intermediates having general formula IV can be prepared according to known methods, refer to U.S. Pat. No. 4,723,034 and U.S. Pat. No. 5,554,578 and so on.

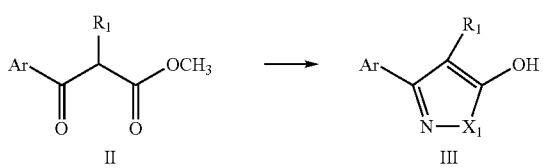

The compounds of the present invention have wide spectrum fungicidal activity, and may be used to control diseases in all sorts of plants caused by oomycete, basidiomycete, ascomycete pathogens and deuteromycete, and it may also provide good control efficacy at very low dosage because of the high activity. These compounds have penetration activity and can be used as soil and foliar fungicides. They can provide satisfied control of cucumber downy mildew, cucumber grey mold, cucumber anthracnose, cucumber powdery mildew, tomato early blight, tomato late blight, phytophthora blight of pepper, grape downy mildew, grape white rot, apple ring rot, apple alternaria leaf spot, rice sheath blight, rice blast, wheat leaf rust, wheat leaf blotch, wheat powdery mildew, rapesclerotiniose, corn southern leaf blight.

Some of the compounds of the present invention have very good insecticidal and acaricidal activity, and may be used to control insects and mites.

The present invention also provides a composition of insecticides and fungicides, the active ingredients of the composition are the compounds having general formula I and their carrier acceptable in agriculture, wherein the active ingredients being present in a total amount of 0.1 to 99% by weight.

The present invention, further more provides preparation method of the said composition thereof. The compounds of general formula I and their carrier are mixed. The said composition may be a single component compound or mixture of compounds with several components of the invention.

Requirements of the carrier in the invention accords: it is easy to apply to the sites being to be treated for the carrier after it is confected with active component. For example, the sites could be plant, seed or soil or places convenient for store, transport or operation. The carrier could de solid or liquid, including the liquid which usually turns from gas condition under pressure. And the carrier(s) being used to confect insecticidal, bactericidal composition are applied.

Suitable solid carrier(s) includes natural or synthetic clays or silicates, for example diatomaceous earths, talcs, magnesium aluminium silicates, aluminium silicates (kaoling), montmorillonites and micas; calcium carbonate; calcium sulphate; ammonium sulphate; synthetic silicon oxides and synthetic calcium silicates or aluminium silicates; elements such as carbon or sulphur; natural and synthetic resins, such as coumarone resins, polyvinyl chloride, or styrene polymers or copolymers; solid polychlorophenols; bitumen; waxes, beeswax or paraffin for instance.

Suitable liquid carriers include water, alcohols such as isopropanol or alcohol; ketones such as acetone, methyl ethyl ketone, methyl isopropy ketone or cyclohexanone; ethers; aromatics such as benzene, toluene, xylene; petroleum fractions such as kerosene or mineral oils; chlorinated aliphatic hydrocarbons such as carbon tetrachloride, tetrachloride ethylene or trichloride ethylene. Mixtures of these different liquids generally are often suitable.

The compositions of insecticides and fungicides are often formulated and transported in a concentrated form which is subsequently diluted by the user before application. The presence of small amounts of surfactant facilitates this process of dilution. Thus preferably at least one carrier in a composition according to the invention is a surfactant. For example the composition may contain at least two carriers, wherein at least one of which is a surfactant.

The surfactant may be an emulsifier, a dispersant or a wetting agent; it may be nonionic or ionic. Examples of suitable surfactant include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycol, sorbic alcohol, sucrose or pentaerythritol and condensations of these with ethylene oxide and/or propylene oxide; condensation products of fatty alcohol or alkyl phenols such as p-octylphenol or p-octylcresol, with ethylene-oxide and/or propylene oxide; sulphates or sulphonates of these condensation products; alkaline metal salts or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate.

Examples of compositions and formulations according to the invention are wettable powder, dustable powder, granule, aqueous solution, emulsifiable concentrate, emulsion, suspension concentrate, aerosol composition or fumigant. Wettable powder usually contains 25, 50 or 75% by weight of active ingredient and usually contain in addition to solid inert carrier, 3-10% weight of a dispersant and, where necessary, 0-10% weight of stabiliser(s) and/or other additives such as penetrants or stickers. Dustable powder are usually formulated as a dust concentrate having a similar composition to that of a wettable powder but a dispersant, and are diluted further with solid carrier to give a composition usually containing 0.5-10% weight of active ingredient. Granules are usually prepared to have a size between 10 and 100 BS mesh (1.676-0.152 mm), and may be manufactured by agglomeration or impregnation techniques. Generally, granules contain 0.5-75% w active ingredient and 0-10% weight of additives such as stabilisers, surfactants, slow release modifiers.

The so-called "dry flowable powders" consist of relatively small granules having a relatively high concentration of active ingredient. Emulsifiable concentrates usually contain, in addition to a solvent and, when necessary, co-solvent, 1-50% weight/volume (w/v) active ingredient, 2-20% w/v emulsifiers and 0-20% w/v of other additives such as stabilisers, penetrants and corrosion inhibitors. Suspension concentrates are usually contain 10-75% weight active ingredient, 0.5-15% weight of dispersing agents, 0.1-10% weight of other additives such as defoamers, corrosion inhibitors, stabilisers, penetrants or stickers.

Aqueous dispersant and emulsions, for example compositions obtained by diluting a wettable powder or a concentrate according to the invention with water, also lie within the scope of the invention. The said emulsions may be of the water-in-oil or of the oil-in-water type.

The composition to which one or more other fungicides are added has wider spectrum activity than single compound having general formula I. In addition, other fungicides may have synergistic effect on the fungicidal activity of the compound having general formula I. The compound having general formula I can also be used with other insecticides, or with another fungicide and other insecticides simultaneously.

DESCRIPTION OF THE INVENTION IN DETAIL

The following examples are illustrative of the present invention.

Preparation Example

Example 1

The Preparation of Compound 2

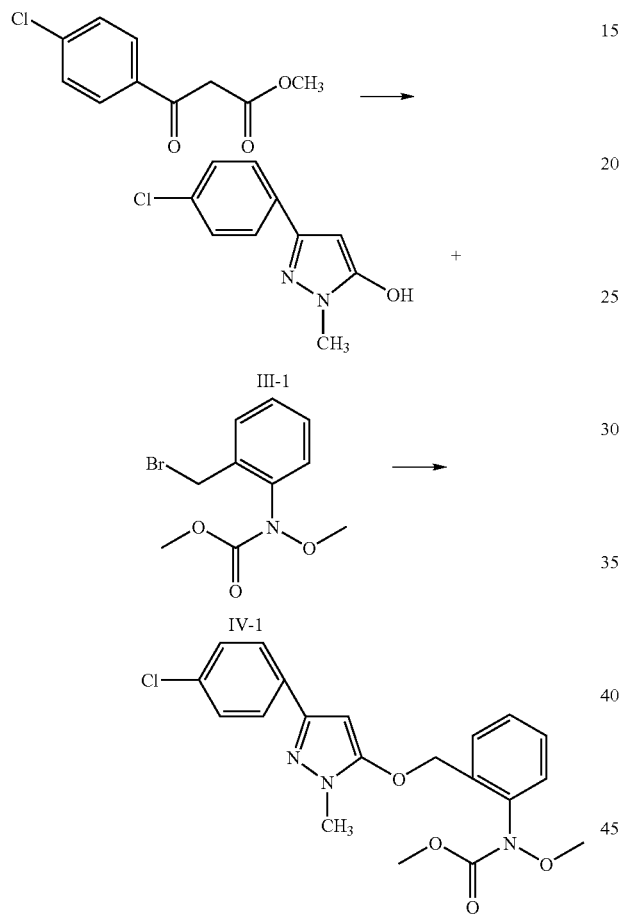

Example 2

The Preparation of Compound 21

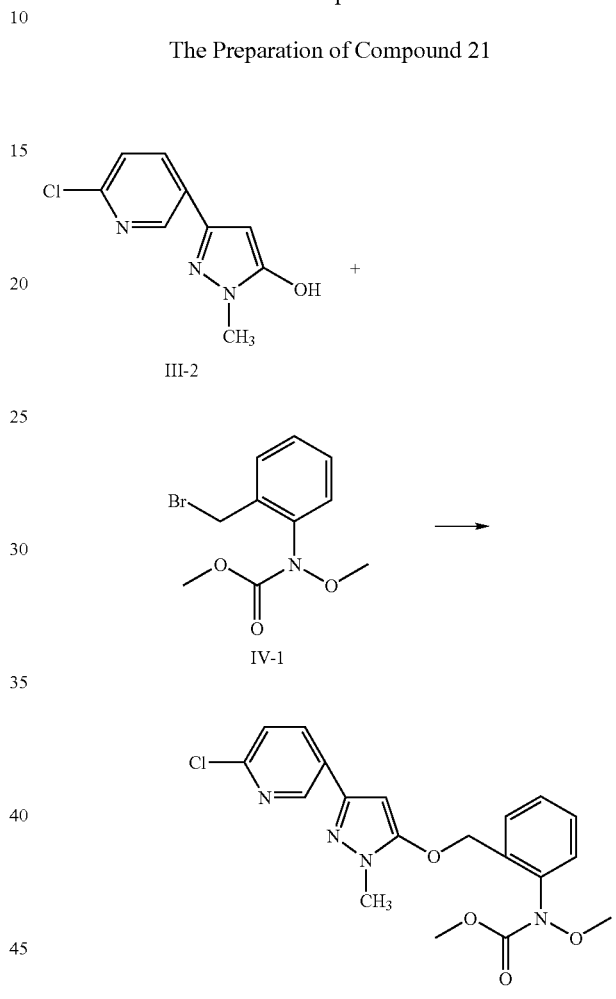

2.12 g of methyl 3-(4-chlorophenyl)-3-oxopropanoate was dissolved in 10 ml of methanol, the solution was heated to reflux. Slightly excessive methyl hydrazine was added to the solution dropwisely, 3 hours later, the reaction was traced by Thin-Layer Chromatography, after the reaction, the solution was condensed, cooled, crystal obtained, and filtrated. The residue was washed with methanol and dried, 1.5 g crystal of 3-(4-chlorophenyl)-1-methyl-1H-pyrazol-5-ol (compound III-1) was obtained.

0.5 g of the above crystal was dissolved in 5 ml of DMF, and 0.17 g of NaH was added to the solution. Then the solution was stirred for 30 min. 0.72 g of compound IV-1 was added, the mixture was stirred and heated to 40° C. 3 hr later, the reaction was traced by Thin-Layer Chromatography, after the reaction, the reaction mixture was poured into 50 ml saturated brine, extracted with 60 ml ethyl acetate 3 times. The combined organic extracts were dried, and concentrated. This was subjected to silica gel column chromatography, to obtain 0.56 g of oil (compound 2).

$^1$HNMR spectrum ($^1$HNMR, 300 Hz, internal standard: TMS, solvent CDCl$_3$) is as follows:

δppm 3.75 (6H, s), 3.81 (3H, s), 5.20 (2H, s), 5.86 (1H, s), 7.35 (2H, d), 7.44 (3H, m), 7.54 (1H, m), 7.69 (2H, m).

0.15 g of NaH (60% pure) was charged in a flask, washed with petroleum ether, 5 ml of DMF and 1.0 g of compound III-2 (prepared according to CN1257490A). After stirred at room temperature for 2 min, 1.4 g of compound IV-1 was added, the reaction temperature was rised to 60° C. 2 hr later, the reaction was traced by Thin-Layer Chromatography, after the reaction, the reaction mixture was poured into 50 ml saturated brine, extracted with 100 ml ethyl acetate 3 times. The combined organic extracts were dried, and concentrated. The crude product was purified through silica gel column and 0.95 g of oil (compound 21) was obtained.

$^1$HNMR spectrum ($^1$HNMR, 300 Hz, internal standard: TMS, solvent CDCl$_3$) is as follows:

δppm 3.75 (3H, s), 3.76 (3H, s), 3.82 (3H, s), 5.21 (2H, s), 5.89 (1H, s), 7.33 (1H, d), 7.45 (3H, m), 7.58 (1H, d), 8.06 (1H, d), 8.68 (1H, s).

Example 3

The Preparation of Compound 89

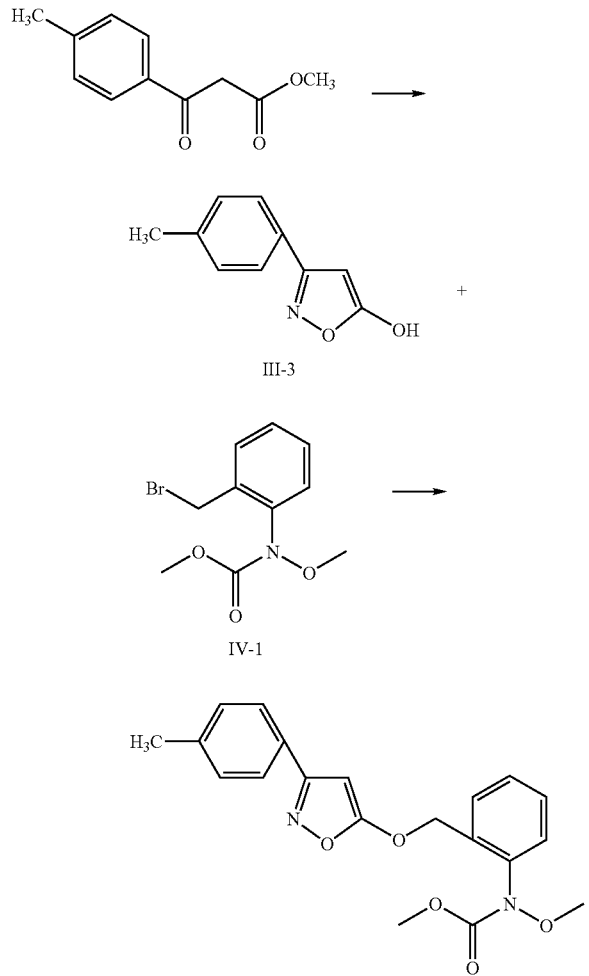

According to method of U.S. Pat. No. 3,781,438, 2 g of methyl 3-(4-methylphenyl)-3-oxopropanoate was dissolved in methanol, slightly excessive hydroxylamine hydrochloride and equivalent amount of sodium hydroxide were added, the mixture was heated to reflux. 3 hr later, the reaction was traced by Thin-Layer Chromatography, after the reaction, water was added to the reaction mixture, extracted with ethyl acetate, The combined organic extracts were dried and concentrated to obtain 3-(4-methylphenyl)isoxazol-5-ol as solid (compound III-3).

1 g of the above compound III-3 was dissolved in DMF, and 0.45 g of NaH_was added to the solution, then the solution was stirred for 30 min. 1.7 g of compound IV-1 was added, the mixture was heated to 50° C. and stirred for 6 hr, the reaction was traced by Thin-Layer Chromatography, after the reaction, the reaction mixture was poured into 50 ml saturated brine, extracted with 100 ml ethyl acetate 3 times. The combined organic extracts were dried, and concentrated, the crude product was purified through silica gel column to obtain 1.5 g of oil (compound 99).

Example 4

The Preparation of Compound 121

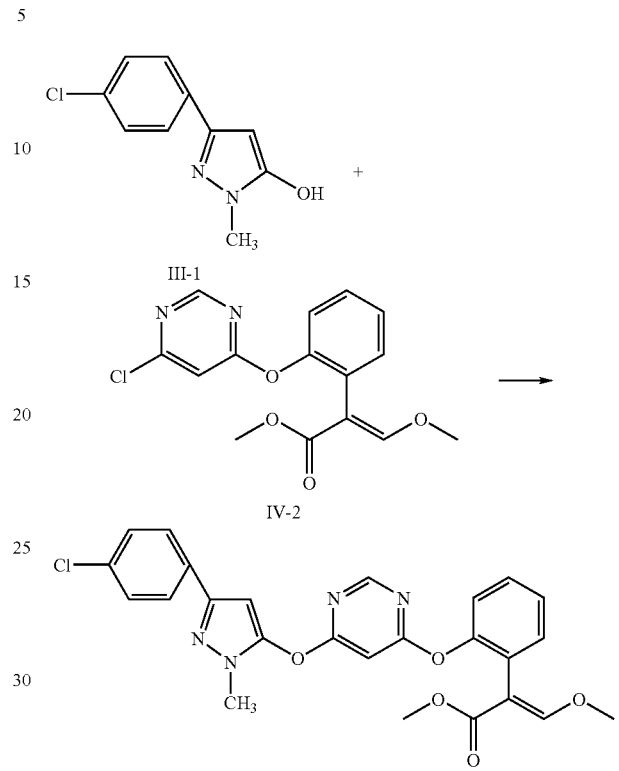

1.0 g of compound III-1, 1.7 g of compound IV-2 (prepared according to WO 9807707, WO 9208703), 2.1 g of potassium carbonate were add in 15 ml DMF, and the reaction mixture was heated to 70-80° C., 7 hr later, the reaction was traced by Thin-Layer Chromatography, after the reaction turnover, the reaction mixture was poured into 100 ml saturated brine, extracted with 100 ml ethyl acetate for 3 times. The combined organic extracts were dried, and concentrated, the crude product was purified through silica gel column to obtain 1.1 g of oil (compound 121).

Other compounds were prepared according the above examples.

Physical and chemical property and $^1$HNMR spectrum ($^1$HNMR, 300 Hz, internal standard:TMS, solvent $CDCl_3$) of some compounds having the general formula I in table 1 of this invention are as follows:

Compound 1: oil. δppm 3.75 (6H, s), 3.81 (3H, s), 5.19 (2H, s), 5.86 (1H, s), 7.40 (5H, m), 7.60 (1H, m), 7.68 (2H, d).

Compound 8: m.p. 98-100° C. δppm 2.47 (3H, s), 3.73 (3H, s), 3.75 (3H, s), 3.81 (3H, s), 5.18 (2H, s), 5.83 (1H, s), 7.24 (1H, m), 7.42 (3H, m), 7.65 (3H, m).

Compound 10: m.p. 89-91° C. δppm 3.75 (6H, s), 3.79 (3H, s), 5.20 (2H, s), 6.07 (1H, s), 7.24 (2H, d), 7.42 (4H, m), 7.58 (1H, m), 7.75 (1H, d).

Compound 11: oil. δppm 1.45 (6H, s), 3.60 (3H, s), 3.66 (3H, s), 4.94 (2H, s), 7.22 (3H, m), 7.30 (3H, m), 7.47 (3H, m).

Compound 12: oil. δppm 3.73 (3H, s), 3.75 (3H, s), 3.81 (3H, s), 3.82 (3H, s), 5.18 (2H, s), 5.79 (1H, s), 6.90 (2H, m), 7.42 (3H, m), 7.61 (1H, m), 7.66 (2H, m).

Compound 15: m.p. 90-92° C. δppm 3.73 (3H, s), 3.75 (3H, s), 3.81 (3H, s), 5.18 (2H, s), 5.83 (1H, s), 7.43 (3H, m), 7.47 (1H, m), 7.50 (1H, m), 7.60 (3H, m).

Compound 16: m.p. 93-95° C. δppm 2.36 (3H, s), 3.74 (3H, s), 3.76 (3H, s), 3.82 (3H, s), 5.19 (2H, s), 5.83 (1H, s), 7.19 (2H, d), 7.42 (3H, m), 7.63 (3H, d).

Compound 17: oil. δppm 1.27 (3H, t), 1.89 (3H, s), 2.70 (2H, q), 3.62 (3H, s), 3.78 (6H, s) 5.32 (2H, s), 7.22 (2H, m), 7.28 (2H, m), 7.40 (3H, m), 7.70 (1H, m).

Compound 20: oil. δppm 3.57 (6H, s), 3.79 (6H, s), 5.26 (2H, s), 5.73 (1H, s), 7.37 (6H, m), 7.50 (1H, m), 7.69 (1H, d).

Compound 26: m.p. 114-116° C. δppm 3.75 (6H, s), 3.81 (3H, s), 4.79 (2H, t), 5.21 (2H, s), 5.83 (1H, s), 7.44 (3H, m), 7.58 (1H, d), 8.06 (1H, dd), 8.44 (1H, s).

Compound 28: oil. δppm 3.72 (3H, s), 3.75 (3H, s), 3.82 (3H, s), 5.17 (2H, s), 5.78 (1H, s), 6.43 (1H, dd), 6.58 (1H, m), 7.41 (4H, m), 7.59 (1H, m).

Compound 29: oil. δppm 3.69 (3H, s), 3.74 (3H, s), 3.81 (3H, s), 5.16 (2H, s), 5.70 (1H, s), 6.82 (1H, m), 6.98 (1H, m), 7.42 (3H, m), 7.56 (1H, m).

Compound 31: oil. δppm 3.73 (3H, s), 3.76 (3H, s), 3.82 (3H, s), 5.18 (2H, s), 5.78 (1H, s), 7.01 (1H, m), 7.20 (1H, m), 7.24 (1H, d), 7.42 (3H, m), 7.60 (1H, m).

Compound 63: m.p. 66-68° C. δppm 1.90 (3H, s), 3.62 (3H, s), 3.79 (6H, s), 5.32 (2H, s), 7.30 (2H, d), 7.42 (6H, m), 7.72 (1H, d), 7.60 (3H, m).

Compound 64: oil. δppm 1.68 (3H, s), 3.60 (3H, s), 3.79 (6H, s), 5.30 (2H, s), 7.25 (2H, d), 7.42 (5H, m), 7.72 (1H, d).

Compound 74: oil. δppm 1.88 (3H, s), 3.61 (3H, s), 3.78 (3H, s), 3.79 (3H, s), 3.86 (3H, s), 5.32 (2H, s), 6.99 (2H, m), 7.22 (2H, m), 7.40 (3H, m), 7.69 (1H, m).

Compound 78: oil. δppm 1.89 (3H, s), 2.05 (3H, s), 3.61 (3H, s), 3.78 (6H, s), 5.31 (2H, s), 7.22 (2H, d), 7.29 (1H, d), 7.38 (3H, m), 7.71 (1H, m).

Compound 107: oil. δppm 2.39 (3H, s), 3.74 (3H, s), 3.76 (3H, s), 3.83 (3H, s), 5.32 (2H, s), 5.56 (1H, s), 7.24 (2H, d), 7.42 (3H, m), 7.63 (3H, d).

Compound 185: oil. δppm 3.61 (3H, s), 3.78 (6H, s), 6.41 (2H, s), 7.20 (1H, m), 7.35 (5H, m), 7.42 (1H, m), 7.72 (2H, d), 8.50 (1H, s).

Compound 194: oil. δppm 1.50 (6H, s), 3.61 (3H, s), 3.77 (6H, s), 6.32 (1H, s), 7.40 (1H, s), 7.20 (1H, m), 7.34 (6H, m), 7.48 (1H, s), 7.74 (2H, d), 8.50 (1H, s).

Compound 199: m.p. 142-144° C. δppm 2.37 (3H, s), 3.61 (3H, s), 3.77 (6H, s), 6.39 (2H, dd), 7.19 (3H, d), 7.38 (2H, m), 7.42 (1H, m), 7.46 (1H, s), 7.68 (2H, d), 8.50 (1H, s).

Compound 204: oil. δppm 3.62 (3H, s), 3.78 (6H, s), 6.43 (2H, m), 7.19 (1H, d), 7.38 (4H, m), 7.48 (1H, s), 8.08 (1H, d), 8.50 (1H, s), 8.78 (1H, s).

Compound 367: m.p. 130-132° C. δppm 3.69 (3H, s), 3.71 (3H, s), 3.84 (3H, s), 5.03 (2H, s), 5.72 (1H, s), 6.43 (1H, dd), 6.61 (1H, dd), 7.17 (1H, m), 7.38 (1H, m), 7.48 (1H, m), 7.61 (1H, s).

Compound 368: m.p. 92-94° C. δppm 3.65 (3H, s), 3.71 (3H, s), 3.83 (3H, s), 5.01 (2H, s), 5.62 (1H, s), 6.81 (1H, d), 6.98 (1H, d), 7.20 (1H, m), 7.37 (2H, m), 7.48 (1H, m), 7.60 (1H, s).

Compound 370: m.p. 96-98° C. δppm 3.69 (3H, s), 3.71 (3H, s), 3.84 (3H, s), 5.03 (2H, s), 5.70 (1H, s), 7.02 (1H, m), 7.21 (2H, m), 7.27 (1H, m), 7.29 (2H, m), 7.38 (1H, m), 7.61 (1H, s).

Compound 391: m.p. 127-130° C. δppm 3.65 (3H, s), 3.85 (3H, s), 4.06 (3H, s), 5.00 (2H, s), 5.86 (1H, s), 7.02 (1H, m), 7.21 (3H, m), 7.48 (3H, m).

Compound 392: oil. δppm 3.72 (3H, s), 3.84 (3H, s), 4.04 (3H, s), 5.02 (2H, s), 5.60 (1H, m), 6.94 (1H, m), 7.21 (1H, m), 7.46 (4H, m).

Compound 394: m.p. 88-90° C. δppm 3.68 (3H, s), 3.85 (3H, s), 4.06 (3H, s), 5.01 (2H, s), 5.73 (1H, s), 6.42 (1H, m), 6.62 (2H, m), 7.25 (1H, m), 7.41 (2H, m), 7.46 (1H, m).

Compound 415: m.p. 139-141° C. δppm 2.92 (3H, d), 3.64 (3H, s), 3.96 (3H, s), 5.00 (2H, s), 5.74 (1H, s), 6.79 (1H, bs), 7.02 (1H, m), 7.22 (3H, m), 7.45 (2H, m), 7.49 (1H, m).

Compound 418: oil. δppm 2.89 (3H, d), 3.42 (3H, s), 3.94 (3H, s), 5.16 (2H, s), 6.43 (1H, m), 6.79 (1H, bs), 6.96 (1H, m), 7.25 (3H, m), 7.46 (3H, m).

Compound 439: oil. δppm 3.75 (3H, s), 3.77 (3H, s), 3.81 (3H, s), 3.88 (3H, s), 5.20 (2H, s), 6.10 (1H, s), 6.94 (2H, m), 7.26 (1H, m), 7.42 (3H, m), 7.61 (1H, m), 7.87 (1H, m).

Compound 440: oil. δppm 2.39 (3H, s), 2.52 (3H, s), 3.74 (6H, s), 3.80 (3H, s), 5.18 (2H, s), 5.65 (1H, s), 6.92 (1H, s), 7.42 (3H, m), 7.48 (1H, m).

Compound 441: oil. δppm 2.39 (3H, s), 2.51 (3H, s), 3.66 (3H, s), 3.69 (3H, s), 3.81 (3H, s), 5.00 (2H, s), 6.56 (1H, s), 6.86 (1H, s), 7.20 (1H, m), 7.35 (2H, m), 7.50 (1H, m), 7.58 (1H, s).

Compound 442: oil. δppm 3.63 (3H, s), 3.73 (3H, s), 3.85 (3H, s), 3.92 (3H, s), 4.05 (3H, s), 5.00 (2H, s), 5.67 (1H, s), 6.79 (2H, m), 6.92 (2H, m), 7.25 (1H, m).

Formulation Example

Base on 100% Active Ingredient (Weight/Weight %)

Example 5

35% Emulsion Concentrate

| | |
|---|---|
| Compound 2 (97.2%) | 35% |
| Phosphorous acid | 10% |
| Ethylenoxy aliphatic acid glycerin ester | 15% |
| Cyclohexanone | complement to 100% |

Phosphorous acid is dissolved in cyclohexanone, then the compound 2 and ethylenoxy aliphatic acid glycerin ester are added, the emulsifiable in transparent solution is obtained finally.

Example 6

60% Wettable Powders

| | |
|---|---|
| Compound 64 (98.4%) | 60% |
| Sodium dodecylnaphthalenesulfate | 2% |
| Sodium lignosulfonate | 9% |
| Kaolin | complement to 100% |

Compound 64, sodium dodecylnaphthalenesulfate, sodium lignosulfonate and kaolin (all solid components) are well mixed and shattered until the particle size reaches the standard.

Example 7

30% Aqueous Suspension

| | |
|---|---|
| Compound 121 (96.6%) | 30% |
| Sodium dodecylnaphthalenesulfate | 4% |
| Hemicellulose | 2% |

-continued

| | |
|---|---|
| Epoxypropane | 8% |
| Water | complement to 100% |

The mixture of compound 121, 80% of the amount of water should being added and sodium dodecylnaphthalenesulfate are shattered in a mill (1 mm ball). Other components are dissolved in the rest 20% water, and are added under stirring to obtain 30% aqueous suspension.

Example 8

25% Suspension Emulsifier

| | |
|---|---|
| Compound 11 (96.2% pure) | 25% |
| Polyethylenoxyalkyl propyl ether | 2.5% |
| Dodecyl polyethylene phosphate ester | 4% |
| Ethylenoxy aliphatic acid glycerin ester | 2% |
| Calcium dodecylbenzenesulfate | 1.5% |
| Cyclohexanone | 30% |
| Petroleum fractions | complement to 100% |

Compound 11 is dissolved in 80% of the amount of solvent (cyclohexanone and petroleum fractions) should being added, and then emulsifiers (dodecyl polyethylene phosphate ester, ethylenoxy aliphatic acid glycerin ester and calcium dodecylbenzenesulfate) and dispersant (2.5% weight of 2,3-epoxypropyl epoxy alkyl copolymer) are added, the mixture is stirred completely and shattered in a mill (1 mm ball). And the rest 20% solvents are added.

Biological Testing

Example 9

Determination of Fungicidal Activity

Determination of fungicidal activities against plant diseases of selected compounds were carried out by following procedure:

Protectant and curative activity of experimental compounds are tested with whole plants. Technical samples were dissolved in a bit acetone and diluted to required concentration with water containing 0.1% Tween 80. For the protectant method, test solution was sprayed onto potted plant. Pathogen inoculation was carried out after 24 hours then plants were hold in growth chambers containing constant temperature and moisture for effect. When untreated plant was under desirable disease severity (after 1 week approximately), assessment were carried out by visual observation. Test plant inoculated with fungus for 4 days are sprayed with the solution of a compound and then cultured in green house for 3-4 days. The curative activity is assessed based on the control plant's index of disease.

Part of the Test Results:

At 500 mg/L, compound 16 showed 100% control against wheat powdery mildew (*BLumeria graminis*), compound 1, 15, 26, 185, 367 showed more than 80%.

At 500 mg/L, compound 1, 8, 15, 194, 367, 415 showed 100% control against cucumber downy mildew (*Pseudoperonospora cubenis*), compound 11, 391 showed 90%.

At 500 mg/L, compound 21 showed 100% control against cucumber grey mold (*Botrytis cinerea*) and wheat powdery mildew.

At 500 mg/L, compound 10, 20, 63, 78 showed 100% control against cucumber downy mildew and wheat powdery mildew.

At 25 mg/L, compound 15, 20, 63, 78 showed 100% control against cucumber downy mildew. At 12.5 mg/L, they showed more than 95% control against wheat powdery mildew.

At 100 mg/L, compound 63 showed 100% control against cucumber anthracnose (*Colletotrichum lagenarium*) and at 1.56 mg/L it still showed 100%.

Compound 63 showed excellent activity against rice blast (*Pyricularia oryzae*), tomato late blight (*Phytophthora infestans*), cucumber downy mildew (*Pseudoperonospora cubensis*), wheat powdery mildew (*Erysiphe graminis*), cucumber anthracnose (*Colletotrichum lagenarium*), cucumber powdery mildew (*Sphaerotheca fuliginea*), rice sheath blight (*Rhizoctonia solani*), and showed good activity on cucumber scab (*Cladosporium cucumerinum*), apple alternaria rot (*valsa mali*) rape sclerotinia stem rot (*Sclerotinia sclerotiorum*), and showed moderate activity against tomato cercospora leaf mold (*Fulvia fulva*), corn southern leaf blight (*Helminthosporium maydis*), wheat head blight (*Fusarium graminearum*).

The results of compound 63 against rice sheath blight and wheat powdery mildew are listed in table 2~4.

TABLE 2 the results of compound 63 against rice sheath blight 1 day protection activity (%)

| compound | 100 mg/L | 50 mg/L | 25 mg/L | 12.5 mg/L | 6.25 mg/L | 3.125 mg/L | 1.5625 mg/L |
|---|---|---|---|---|---|---|---|
| 63 | 100 | 100 | 80 | 75 | 65 | 60 | 55 |
| triophanate-methyl | 75 | 55 | 20 | 0 | 0 | 0 | 0 |

TABLE 3 the results of compound 63 against wheat powdery mildew 1 day protection activity (%)

| compound | 25 mg/L | 12.5 mg/L | 6.25 mg/L | 3.125 mg/L | 1.56 mg/L | 0.78 mg/L | 0.39 mg/L | 0.19 mg/L |
|---|---|---|---|---|---|---|---|---|
| 63 | 100 | 100 | 100 | 100 | 100 | 95 | 75 | 55 |
| Kresoxim methyl | 100 | 100 | 98 | 70 | 40 | 15 | 0 | — |

TABLE 4 the results of compound 63 against wheat powdery mildew 4 day curative activity (%)

| compound | 12.5 mg/L | 6.25 mg/L | 3.125 mg/L | 1.56 mg/L | 0.78 mg/L | 0.39 mg/L |
|---|---|---|---|---|---|---|
| 63 | 100 | 100 | 100 | 100 | 80 | 50 |
| tebuconazole | 85 | 70 | 45 | 15 | 0 | 0 |
| pyraclostrobin | 100 | 100 | 85 | 60 | 25 | 0 |
| Kresoxim methyl | 100 | 20 | 15 | 10 | 0 | 0 |

Example 10

Determination of Insecticidal and Acaricidal Activity

Determination of insecticidal and acaricidal activities of selected compounds were carried out by following procedure:

Technical samples were dissolved in mixed solvent (acetone:methanol=1:1), and diluted to required concentration with water containing 0.1% of tween 80.

The second instar larvae of armyworm (*Leucania separata*), diamond backmoth (*Plutella xylostella*) and culex mosquitoes (*Culex pipiens pallens*), green peach aphids (*Myzus persicae*) and mite (*Tetranychus cinnabarinus*) were used in biological test. The method was employed either spraying by airbrush or immersing (larvae of culex mosquitoes). A test solution (0.5 mL) was sprayed at the pressure of 10 psi (about 0.7 kg/cm$^2$). Percent mortality was determined after two days.

Part of Test Results:

At 600 mg/L, compound 15, 21, 63, 64 showed more than 85% control of armyworm, diamond backmoth, green peach aphids and culex mosquitoes.

At 200 mg/L, compound 15 showed 90% control of green peach aphids, and compound 63 showed 100% control of diamond backmoth.

We claim:

1. An aryl ether compound having formula (I):

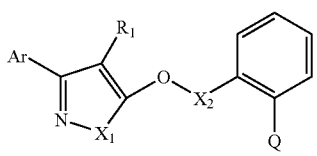

wherein: $X_1$ is $NR_2$;
$X_2$ is $CH_2$;
$R_1$ is selected from H, halo, NO$_2$, CN, CONH$_2$, CH$_2$CONH$_2$, CH$_2$CN, C$_1$-C$_{12}$alkyl, C$_1$-C$_{12}$haloalkyl, C$_1$-C$_{12}$alkoxy, C$_1$-C$_{12}$haloalkoxy, C$_1$-C$_{12}$alkylthio, C$_1$-C$_{12}$alkylsulfonyl, C$_1$-C$_{12}$alkylcarbonyl, C$_1$-C$_{12}$alkoxyC$_1$-C$_{12}$alkyl, C$_1$-C$_{12}$alkoxycarbonyl, C$_1$-C$_{12}$alkoxycarbonylC$_1$-C$_{12}$alkyl, C$_1$-C$_{12}$haloalkoxyC$_1$-C$_{12}$alkyl, substituted or unsubstituted aminoC$_1$-C$_{12}$alkyl;
$R_2$ is selected from H, C$_1$-C$_{12}$alkyl, C$_1$-C$_{12}$haloalkyl, C$_1$-C$_{12}$alkoxycarbonyl or C$_1$-C$_{12}$alkoxycarbonylC$_1$-C$_{12}$alkyl;
Q is

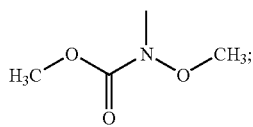

Ar is selected from substituted or unsubstituted aryl, heteroaryl; the substitution group is selected from halo, CN, NO$_2$, C$_1$-C$_6$alkyl, C$_1$-C$_6$alkoxy, C$_1$-C$_6$ alkylthio, C$_1$-C$_6$alkylsulfonyl, C$_1$-C$_6$alkoxycarbonyl, C$_1$-C$_6$haloalkoxy, substituted aryl or substituted aroxyl; and stereoisomers thereof.

2. The compound according to the claim 1, wherein formula (I):

$R_1$ is selected from H, halo, NO$_2$, CN, CONH$_2$, CH$_2$CONH$_2$, CH$_2$, CH$_2$CN, C$_1$-C$_6$alkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfonyl, C$_1$-C$_6$alkylcarbonyl, C$_1$-C$_6$alkoxyC$_1$-C$_6$alkyl, C$_1$-C$_6$alkoxycarbonyl, C$_1$-C$_6$alkoxycarbonylC$_1$-C$_6$alkyl, C$_1$-C$_6$haloalkoxyC$_1$-C$_6$alkyl, substituted or unsubstituted aminoC$_1$-C$_6$alkyl;

$R_2$ is selected from H, C$_1$-C$_6$alkyl, C$_1$-C$_6$haloalkyl, C$_1$-C$_6$alkoxycarbonyl or C$_1$-C$_6$alkoxycarbonylC$_1$-C$_6$alkyl; and Ar is selected from substituted or unsubstituted aryl, heteroaryl; the substitution group is selected from halo, CN, NO$_2$, C$_1$-C$_6$alkyl, C$_1$-C$_6$alkoxy, C$_1$-C$_6$ alkylthio C$_1$-C$_6$ alkylsulfonyl, C$_1$-C$_6$alkoxycarbonyl, C$_1$-C$_6$haloalkoxy, substituted phenyl or substituted phenoxy.

3. The compound according to the claim 2, wherein formula (I):

$R_1$ is selected from H, halo, NO$_2$, CN, CONH$_2$, CH$_2$CONH$_2$, CH$_2$CN, C$_1$-C$_6$alkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfonyl, C$_1$-C$_6$alkylcarbonyl, C$_1$-C$_6$alkoxyC$_1$-C$_6$alkyl, C$_1$-C$_6$alkoxycarbonyl, C$_1$-C$_6$alkoxycarbonylC$_1$-C$_6$alkyl, C$_1$-C$_6$haloalkoxyC$_1$-C$_6$alkyl, substituted or unsubstituted aminoC$_1$-C$_3$ alkyl;

$R_2$ is selected from H, C$_1$-C$_6$alkyl, C$_1$-C$_6$haloalkyl, C$_1$-C$_3$alkoxycarbonyl or C$_1$-C$_6$alkoxycarbonylC$_1$-C$_3$ alkyl; and Ar is selected from substituted or unsubstituted phenyl, pyridine, furan, thiophen or thiazol; the substitution group is selected from halo, CN, NO$_2$, C$_1$-C$_6$alkyl, C$_1$-C$_6$alkoxy, C$_1$-C$_6$alkylthio, C$_1$-C$_6$alkylsulfonyl, C$_1$-C$_6$haloalkoxy, substituted phenyl or substituted phenoxy.

4. The compound according to the claim 3, wherein formula (I):

$R_1$ is selected from H, Cl, Br, F, NO$_2$, CH$_2$CN or C$_1$-C$_6$alkyl;

$R_2$ is selected from H, C$_1$-C$_3$alkyl, C$_1$-C$_3$haloalkyl, C$_1$-C$_3$alkoxycarbonyl or C$_1$-C$_3$alkoxycarbonylC$_1$-C$_3$alkyl; and Ar is selected from substituted or unsubstituted phenyl, pyridine, furan, thiophen or thiazol; the substitution group is selected from halo, CN, NO$_2$, C$_1$-C$_6$alkyl, C$_1$-C$_6$alkoxy, C$_1$-C$_6$alkylthio, C$_1$-C$_6$haloalkoxy, chloro phenyl or chloro phenoxy.

5. The compound according to the claim 4, wherein formula (I):

$R_1$ is selected from H or methyl;

$R_2$ is selected from H, methyl or isopropyl; and

Ar is selected from substituted or unsubstituted phenyl, pyridine, furan or thiophen, the substitution group is selected from halo, C$_1$-C$_3$alkyl, C$_1$-C$_3$alkoxy, C$_1$-C$_3$alkylthio or C$_1$-C$_3$haloalkoxy.

6. The compound according to the one of claims 1-5, wherein the compound having formula (I) is prepared by reaction an azole compound containing a hydroxy group having general formula (III) with halomethylbenzene having formula (IV) at the present of base:

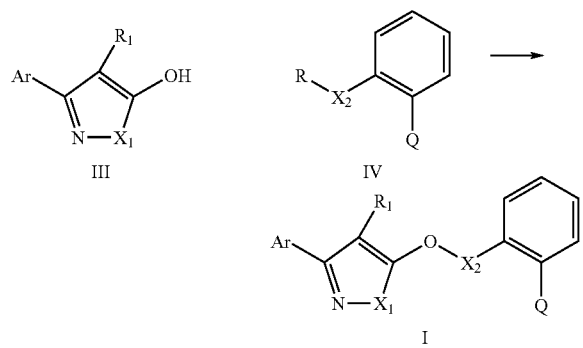

wherein: R is leaving group.

7. A method of controlling insects in a plant which comprises contacting the compound according to claim 1 with the plant.

8. A method of controlling fungi in a plant which comprises contacting the compound according to claim 1 with the plant.

9. A composition for controlling insects or fungi which comprises the compound according to any one of claims 1-5 as an active ingredient, wherein the weight percentage of the active ingredient in the composition is from 0.1% to 99%.

* * * * *